United States Patent
Wehlan et al.

(10) Patent No.: US 10,696,633 B2
(45) Date of Patent: Jun. 30, 2020

(54) PROCESS FOR THE PREPARATION OF FEXOFENADINE AND OF INTERMEDIATES USED THEREIN

(71) Applicant: SANOFI-AVENTIS DEUTSCHLAND GMBH, Frankfurt am Main (DE)

(72) Inventors: Hermut Wehlan, Frankfurt am Main (DE); Kai Rossen, Frankfurt am Main (DE); Guenter Billen, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 15/769,661

(22) PCT Filed: Oct. 21, 2016

(86) PCT No.: PCT/EP2016/075391
§ 371 (c)(1),
(2) Date: Oct. 11, 2018

(87) PCT Pub. No.: WO2017/068219
PCT Pub. Date: Apr. 27, 2017

(65) Prior Publication Data
US 2018/0297951 A1    Oct. 18, 2018

(30) Foreign Application Priority Data

Oct. 22, 2015  (EP) .................................... 15191020

(51) Int. Cl.
*C07D 211/34*  (2006.01)
*C07D 211/22*  (2006.01)

(52) U.S. Cl.
CPC .......... *C07D 211/34* (2013.01); *C07D 211/22* (2013.01)

(58) Field of Classification Search
CPC .................................................. C07D 211/22
See application file for complete search history.

(56) References Cited

U.S. PATENT DOCUMENTS

| | | | |
|---|---|---|---|
| 2,804,422 A | 8/1957 | Schumann et al. | |
| 4,254,129 A | 3/1981 | Carr et al. | |
| 5,750,703 A | 5/1998 | D Ambra | |
| 6,242,606 B1 * | 6/2001 | Krauss ..................... | C07C 33/46 546/239 |
| 6,340,761 B1 | 1/2002 | Krauss et al. | |
| 6,348,597 B2 | 2/2002 | Krauss et al. | |
| 10,336,698 B2 * | 7/2019 | Wehlan .................. | C07C 253/30 |
| 2003/0105329 A1 | 6/2003 | Schroeder et al. | |

FOREIGN PATENT DOCUMENTS

| | | | | |
|---|---|---|---|---|
| IN | 2620/CHE/2013 | * | 3/2015 | ........... C07D 473/16 |
| WO | WO-1995/00482 A1 | | 1/1995 | |
| WO | WO-2002/010115 A1 | | 2/2002 | |
| WO | WO-2003/000658 A1 | | 1/2003 | |
| WO | WO-2006/034092 A2 | | 3/2006 | |
| WO | WO-2006/034092 A3 | | 3/2006 | |
| WO | WO-2007/135693 A2 | | 11/2007 | |
| WO | WO-2007/135693 A3 | | 11/2007 | |

OTHER PUBLICATIONS

Fang, Q.K. et al. (1998). "An Efficient and Facile Synthesis of Racemic and Optically Active Fexofenadine," *Tetrahedron Letters* 39:2701-2704.

Hardouin, C. et al. (2007; e-published on Jun. 9, 2007). "Structure—Activity Relationships of α-Ketooxazole Inhibitors of Fatty Acid Amide Hydrolase," *Journal of Medicinal Chemistry* 50(14):3359-3368.

Huang, J. et al. (Nov. 19, 2010, e-pub. Oct. 4, 2010). "Novel Preparation of $H_1$ Receptor Antagonist Fexofenadine," *Organic Process Research & Development* 14(6):1464-1468.

Pocar, D. et al. (Dec. 1975). "Enamines—XXXIX: Enamines from Cyclopropylketones," *Tetrahedron* 31(19):2427-2429.

Shanklin, Jr., J.R. et al. (1991). "Synthesis, Calcium-Channel-Blocking Activity, and Antihypertensive Activity of 4-(Diarylmethyl)-1-[3-(aryloxy)propyl]piperidines and Structurally Related Compounds," *J. Med. Chem.* 34(10):3011-3022.

Shi, M. et al. (Jul. 2004, e-pub. Jan. 7, 2004). "Reactions of Cyclopropyl Aryl Ketones with Sulfonamides Mediated by $Zr(OTf)_4$: Cascade Preparation of 5-Aryl-3,4-dihydro-2H-pyrrole," *Synlett* 2004(9):1622-1624.

Walsh, D.A. et al. (1989). "Synthesis and Antiallergy Activity of 4-(Diarylhdroxymethyl)-1-[3-(aryloxy)propyl]piperidines and Structurally Related Compounds," *J. Med. Chem.* 32(1):105:118.

Yovell, J. et al. (Jan. 1, 1977). "Acid-Catalyzed Addition of Secondary Amines to Cyclopropyl Ketones. Mass Spectra of Some Cyclic Aminobutyrophenones," *The Journal of Organic Chemistry* 42(5):850-855.

Zuidema, D.R. et al. (2010; e-published on Mar. 12, 2010). "Novel Method of Reducing Ketones Using Sodium Hydroxide in Isopropanol," *Synthetic Communication* 40(8):1187-1191.

International Preliminary Report on Patentability completed on Sep. 20, 2017 for PCT Application No. PCT/EP2016/075391, filed on Oct. 21, 2016, six pages.

International Search Report dated Nov. 24, 2016 for PCT Application No. PCT/EP2016/075391, filed on Oct. 21, 2016, four pages.

Written Opinion of the International Searching Authority dated Nov. 24, 2016 for PCT Application No. PCT/EP2016/075391 filed on Oct. 21, 2016, six pages.

* cited by examiner

*Primary Examiner* — Noble E Jarrell

(74) *Attorney, Agent, or Firm* — Morrison & Foerster LLP

(57) ABSTRACT

A new process for the preparation of fexofenadine and of related intermediates, which can be used in the preparation of fexofenadine, is provided.

18 Claims, No Drawings

PROCESS FOR THE PREPARATION OF FEXOFENADINE AND OF INTERMEDIATES USED THEREIN

CROSS-REFERENCE TO RELATED APPLICATIONS

This application is a National Phase application under 35 U.S.C. § 371 of International Application No. PCT/EP2016/075391, filed Oct. 21, 2016, which claims priority to European Application No. 15191020.5, filed Oct. 22, 2015, the disclosures of each of which are incorporated herein by reference in their entirety.

BACKGROUND OF THE INVENTION

The present invention relates to a chemical process for the manufacture of fexofenadine or a pharmaceutically acceptable salt thereof, and to the manufacture of certain intermediates needed in said process. Fexofenadine is a compound of formula I

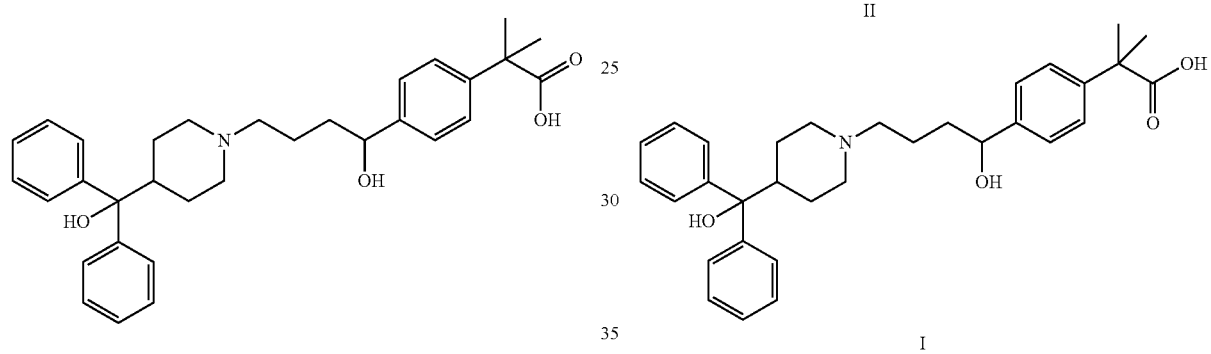

Fexofenadine is an antihistamine pharmaceutical drug for the treatment of allergy symptoms and it is a bronchodilator (U.S. Pat. No. 4,254,129, Richardson-Merrell Inc.).

The general synthesis known for fexofenadine via compounds of formula II and their conversion into fexofenadine is shown in scheme A below. A halogen compound of formula III is alkylated by the compound of formula IV, which is also designated as azacyclonol (U.S. Pat. No. 2,804,422, Merrel), to yield a keto compound of formula II, followed by reduction of the ketone and introduction of the propionic acid functionality either by saponification/hydrolysis (R1=carboxylic ester, amide, nitrile) or introduction of the carbonyl group by oxidation (R1=CH$_2$OR2, R2 is acetyl, benzoyl or hydrogen) or by carbonylation (R1=H), yielding fexofenadine of formula I. The conversion of cyclopropyl aryl ketones V to the required gamma-halo ketones III with acids or Lewis-acids is also described in the literature.

Scheme A

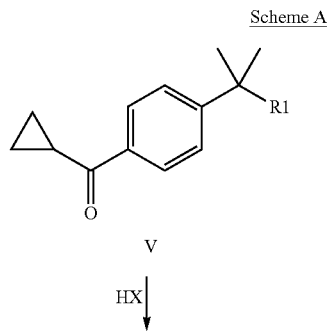

The strategy for using III is described in U.S. Pat. No. 6,340,761 (Merrel), in scheme L and by the examples 43 to 60, where X is chloro and R1 is an ester or an amide functionality. The preparation of a gamma-halo ketone compound of formula III (X is chloro, R1 is COOEt) from the corresponding cyclic precursor V with dry hydrogen chloride is described in column 49, Example 12. The compound of formula V is described and used as one source for making a compound of formula III (e.g. schemes H or I), wherein R1 is a carboxylic acid or a carboxylic acid ester.

A similar compound of formula III (with X=iodide and R1=nitrile) is reported in WO 2002/010115 A1 (Texcontor) where its preparation from the cyclopropyl precursor with trimethylsilyl iodide is described (page 6, example 9).

This approach is also described by Wang et al. (Org. Proc. Res. and Dev. 2010, 14, 1464-68) wherein a compound of formula III (R1 is nitrile) is described and a detailed investigation of its reaction was done with various leaving groups X (X=chloro, bromo or tosylate) with yields of about 30 to 60% under varying conditions (Table 2 in Wang et al., reaction of compounds 6a-d with 7 to form 8 but also 8a). In competition to the desired alkylation compound V is formed as a side product. Product V obtained as side product (compound 8a in Wang et. al) explains the low yield, as it does not react anymore under these reaction conditions for the alkylation of III with IV (Scheme B). This side product V is the result of a cyclisation reaction of compound III which simultaneously competes with the desired bimolecular substitution reaction of III with IV. This cyclisation reaction is independent of the presence and concentration of azacyclonol IV and occurs as a intramolecular ketone alkylation within III which is facile even with weak bases such as NaHCO$_3$ or Et3N as used in Table 2. These reactions are known as being very rapid with reaction rates too fast to be measured easily.

Scheme B

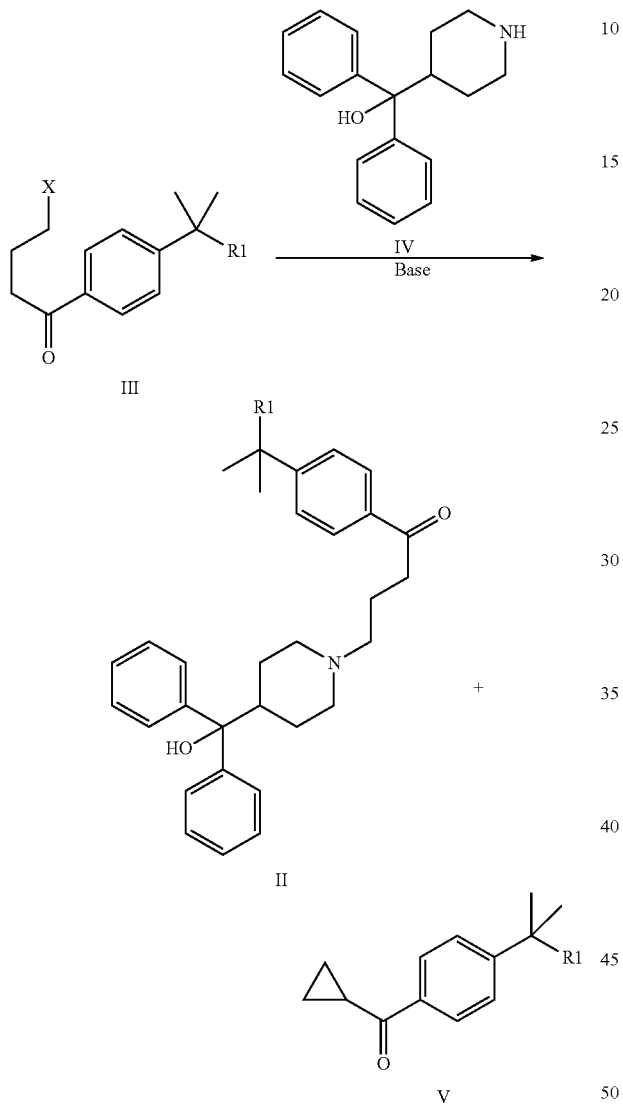

Under the reaction conditions described by Wang compound V is a dead-end product, which does not react further with compound IV and is thus not forming compound II. That indeed a further reaction of V with IV does not take place has been confirmed by the inventors by reacting compound IV with a compound of formula V, wherein R1 is CN, under the various reaction conditions described in Table 2 of Wang et al. (see Reference Example 1 below). Within the limit of detection (<0.1%) no formation of II from V was observed.

Thus, the gamma-halogen compounds of formula III obtained by the cyclopropyl opening of V and subsequently reacted with azacyclonol as shown in scheme A all have the disadvantages described for schemes A and B, namely the facile reverse reaction reforming the dead-end cyclopropyl ketone V by intramolecular ketone alkylation. In addition to the often low yield in the alkylation step the synthesis described for the compounds of formula III involve either long chemical sequences (4-5 steps) which use hazardous, highly toxic and expensive reagents or suffer from low yields and unselective chemical transformations.

Although it would be advantageous only few references deal with the idea of a direct reaction of a compound of formula V with IV in order to obtain a compound of formula II. WO 95/00482 (Albany Mol. Research) or equivalent U.S. Pat. No. 5,750,703 describe the use of substantially pure regioisomers of a compound of formula V (R1 is COOH or COOEt) to make a compound of formula III (X is chloro or iodo) and further a compound of formula II. Moreover, on page 29 and on page 30, lines 1-14 the reaction of these pure regioisomers of V with azacyclonol is described in general terms to be "carried out in a suitable solvent preferably in the presence of a base and optionally in the presence of a Lewis Acid such as magnesium, caesium, or calcium salts or trimethylsilyl chloride or in the presence of a catalytic amount of potassium iodide for about 4 to 120 hours at a temperature . . . " (page 30, lines 1ff.). However, no example is given for this conversion. Indeed, implied in this description is again the synthetically equivalent opening of the cyclopropyl ketone V with the nucleophilic halide under acidic conditions such as the use of TMSCl alone or in the presence of a Lewis acid and possibly potassium iodide, followed by the coupling of the resulting compound III under basic conditions as described by e.g. Huang. Accordingly, it is not apparent for a person skilled in the art, which reaction conditions, if any, are to be chosen which would allow a direct conversion of the acid or ester precursor V to obtain compound II.

WO 03/000658 (Aurobindo Pharma) also claims the conversion of a compound designated formula I

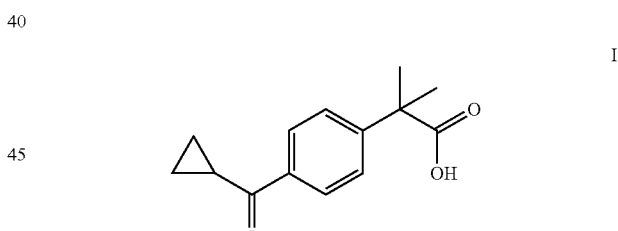

with azacyclonol into II under so called "conditions effective to form the piperidine derivative compound" designated therein as XI (page 5). However, in practice (Example 7) the conditions are again those which first convert the cyclopropyl compound I into a compound of formula III as shown in Schema A (R1 is COOH) which in the subsequent step is coupled with azacyclonol.

WO2006/034092 (AMR technologies) describes the synthesis of fexofenadine in various ways. In scheme 4 (page 26) the reaction of a compound 10 (corresponding to the compound of formula V wherein R1 is COOMe) with azacyclonol is shown wherein the reaction is described to be done in the presence of TsOH. In scheme 3 the publication by Yovell et al. (J. Org. Chem. 42, 850-855, 1977) is referenced for these reaction conditions. However, the reaction was not performed (indicated by broken arrow—see para. 0046/page 20 for explanation; no example given). The cited reference of Yovell et al. itself investigates direct coupling of certain cyclopropyl ketones with secondary amines, such as piperidine (Table I) wherein the reaction is catalyzed by para-toluenesulfonic acid (p-TsOH). The reaction is occurring with overall moderate yield (30-65%) for the three amines used even though both the cyclopropyl ketone and the amines are simple structures compared to azacyclonol IV which contains in addition to the piperidine structure a highly hindered tertiary alcohol which is prone to the elimination of water by an SN1 type mechanism.

Indeed, performing the reaction under the conditions used by Yovell et al. (see Reference Example 2a below) leads to a slow conversion of IV and compound of formula V (R1 is CN) to give II. Using 10 mol % of pTsOH in xylene gave about 50% conversion after 20 hours at reflux. Attempts to increase the rate of the reaction by increasing the amount of catalyst to 1 equiv. of pTsOH resulted in a complete and rapid elimination of water from IV (see Reference Example 2b below). Thus, the rate of conversion and the formation of several impurities demonstrate that the acidic coupling conditions mentioned in WO2006/034092 are actually not suitable for a commercial preparation of II and by inference Fexofenadine.

Few other references describe the direct reaction of certain cyclopropyl aryl ketones being structurally different from V with simple amines to yield the gamma-amino ketones. First reported by Pocar et al. (Tetrahedron 1975, 31, 2427) gamma-amino ketones were obtained in low yield (<20%) from cyclopropyl aryl ketones and secondary amines by titanium tetrachloride catalysis. Using the same catalyst Boger et al. reported 28% yield of a gamma-amino ketone (J. Med. Chem. 2007, 50, 3359). Shi et al. reported the conversion of cyclopropyl aryl ketones with sulphonamides using stoichiometric amounts of Lewis acid catalyst $Zr(OTf)_4$ (Synlett 2004, 1622). All the procedures published are without practical utility for the present problem as they suffer from low yields and expensive catalysts.

WO2007/135693 (IND-SWIFT Laboratories) describes the synthesis of fexofenadine (I) by direct coupling of an appropriately chosen derivative of a compound of formula V where the missing reactivity of V in the coupling with azacyclonol is overcome by the addition of a strongly polarizing and activating ester group on the cyclopropyl ketone by using a compound of formula VI

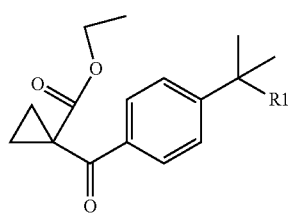

wherein R1 is COOalkyl. The activation is then enabling the direct reaction with azacyclonol to obtain a compound of formula VIII,

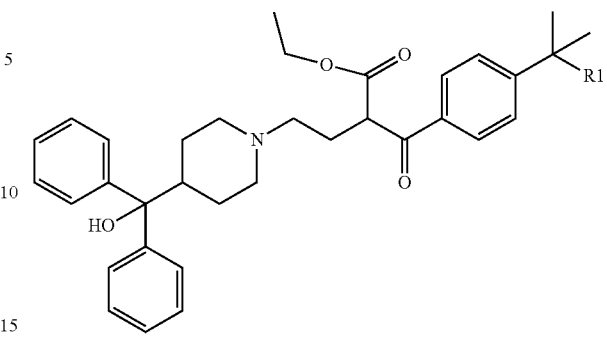

which has not been possible without this activation as described above.

In the example bridging pages 17 and 18 the reaction is described by reacting the ethyl ester with azacyclonol in DMSO at 60-65 degrees Celsius for 48 hours under nitrogen atmosphere. After work up 640 g of the ethylester of a compound of formula VIII was obtained, which, when calculated, corresponds to a yield of about 44%. This low yield is highlighting the challenge of directly opening a cyclopropyl ketone with an amine, even when the cyclopropyl ketone is additionally activated by an ethoxycarbonyl group. In addition to the moderate coupling yield forming VIII, the preparation of VI requires several additional steps and makes this approach less attractive.

In summary, the approach for preparing Fexofenadine by direct coupling of a compound of formula V with azacyclonol is not described in the art in a suitable manner as outlined above. The prior art does not describe or suggest suitable experimental conditions other than use of an acid described above by AMR Technology for coupling V (R1 is COOMe) or using an activated ester derivative of V (R1 is COOEt), both with limited success.

SUMMARY OF THE INVENTION

The present invention provides an alternative process for the preparation of fexofenadine by direct coupling of azacyclonol with a corresponding cyclopropyl aryl ketone to obtain an intermediate which can be further converted into fexofenadine.

DETAILED DESCRIPTION OF THE INVENTION

The known synthesis methods for making fexofenadine, although useful and being applied in practice, still have some drawbacks as indicated before, which, if overcome, would further improve the synthesis. This is important for commercial activities and for minimizing the environmental impact of the practiced chemistry. The present invention solves this problem by providing a process for the direct coupling of a compound of formula V with azacyclonol IV, which results in a shorter synthesis of fexofenadine. Surprisingly it has now been found that the reaction between a compound of formula V and azacyclonol to yield a compound of formula II can be achieved.

In one aspect the present invention relates to a process for the preparation of a compound of formula II

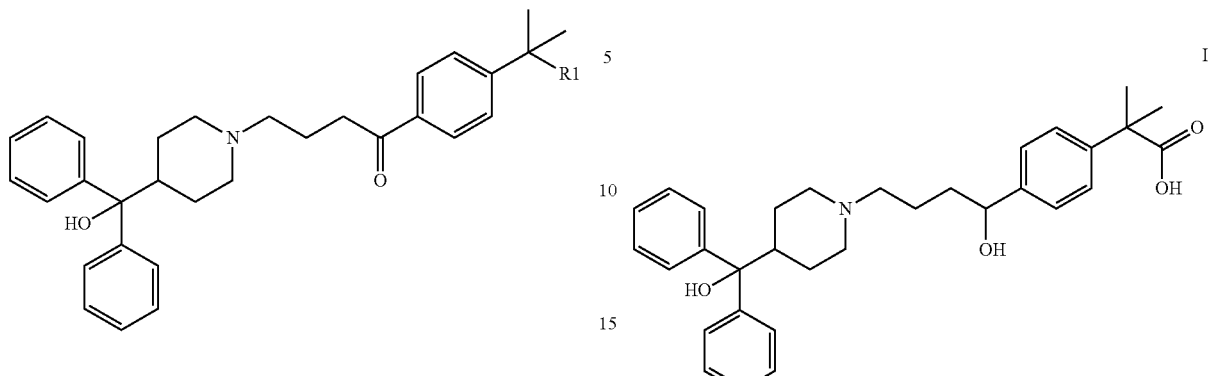

wherein R1 is CN, CONH2, or COOR2, wherein R2 is C1-C4 alkyl,
the process comprises or is characterized by reacting a compound of formula V

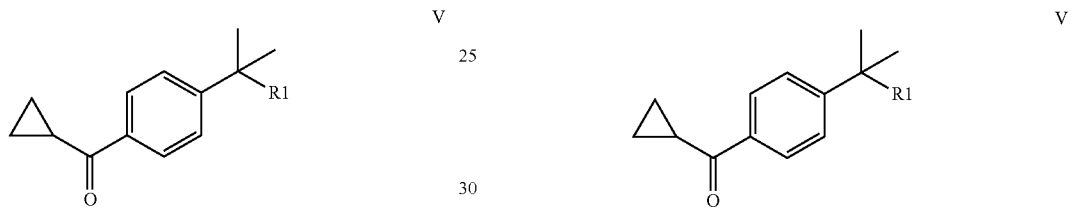

wherein R1 is CN or CONH2 or COOR2, R2 is C1-C4 alkyl, with the compound of formula IV at a temperature above 80° C. without any solvent or optionally in the presence of a small amount of solvent,
and, if R1=CN and CONH2, optionally in the presence of a suitable salt added to the reaction mixture or,
if R1=COOR2, in the presence of a suitable salt added to the reaction mixture, In one embodiment, the process of the present invention further comprises converting the compound of formula II into a compound of formula I or a pharmaceutically acceptable salt thereof.

Accordingly, the present invention also relates to a process for making a compound of formula I or a pharmaceutically acceptable salt thereof,
comprising reacting a compound of formula V wherein R1 is CN or CONH2, or COOR2, wherein R2 is C1-C4 alkyl,
with the compound of formula IV under conditions as further described herein
to yield a compound of formula II

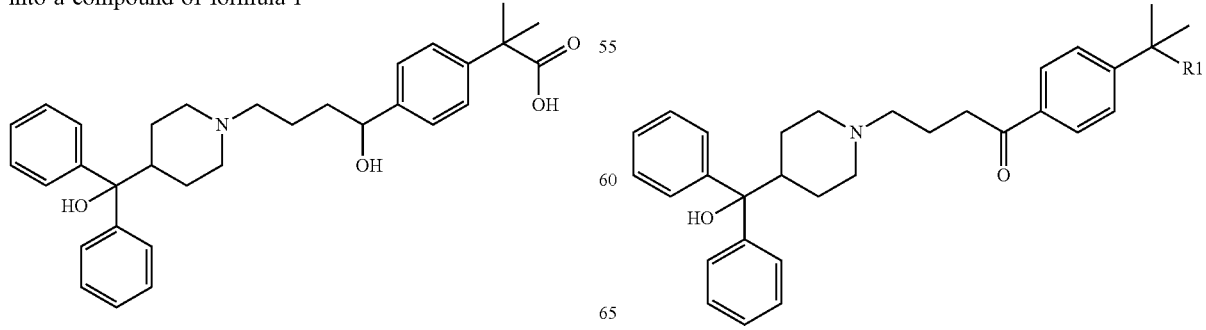

wherein R1 is CN or CONH2 or COOR2, wherein R2 is C1-C4 alkyl, and converting the compound of formula II into a compound of formula I or a pharmaceutically acceptable salt thereof.

C1-C4 alkyl means a linear or branched hydrocarbon, incl. methyl, ethyl, propyl, isopropyl, butyl, 2-methyl-propyl.

In one embodiment of the process of the present invention R1 is CN or CONH2. In a further embodiment R1 is CN. In another embodiment R1 is CONH2. In another embodiment R1 is COOR2. In one embodiment R2 is methyl or ethyl, preferably ethyl.

Nothing in the prior art suggests that high temperature and high concentrations of the compounds to be reacted, i.e. not performing the reaction in solution, would solve the problem of achieving the direct reaction of a compound of formula V with the compound of formula IV in a useful yield and that, additionally, the addition of suitable salts in catalytic amounts would further greatly improve the conversion.

In one embodiment of the process of the present invention R1 is a nitrile. In this embodiment the compound of formula II-A

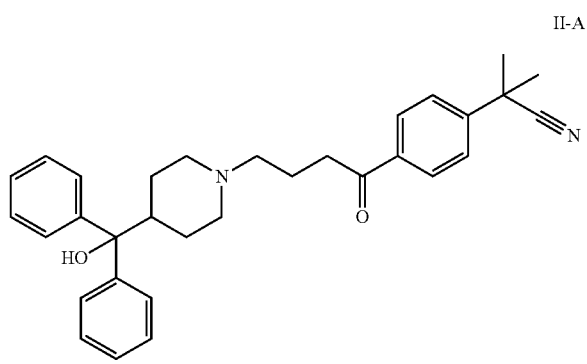 [SMILES: CC(C)(C#N)c1ccc(C(=O)CCCN2CCC(C(O)(c3ccccc3)c3ccccc3)CC2)cc1]

II-A is prepared.

In another embodiment of the present invention R1 is an amide. In this embodiment the compound of formula II-B

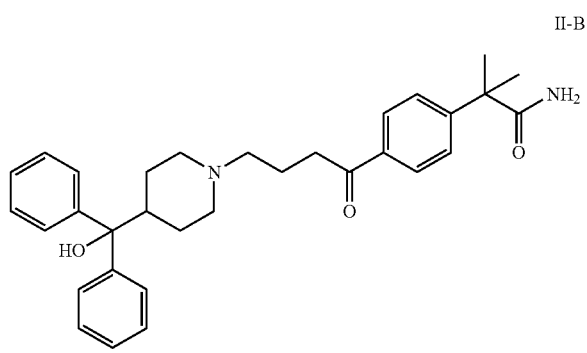 [SMILES: CC(C)(C(N)=O)c1ccc(C(=O)CCCN2CCC(C(O)(c3ccccc3)c3ccccc3)CC2)cc1]

II-B is prepared.

In another embodiment of the process of the present invention R1 is a COOR2. In this embodiment the compound of formula II-C

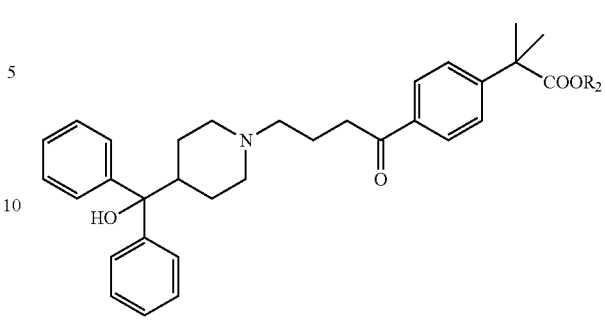

II-C is prepared.

A compound of formula V, wherein R1 is CN, corresponds to the compound of formula V-A (2-[4-(cyclopropanecarbonyl-)-phenyl]-2-methyl-propanenitrile),

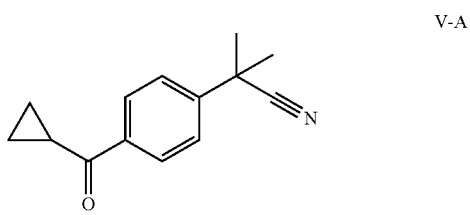 [SMILES: CC(C)(C#N)c1ccc(C(=O)C2CC2)cc1]

V-A

This compound is available according to methods described in the art such as in U.S. Pat. No. 6,340,761 (e.g. Ex. 9). V-A can be further converted into the compound of formula V-B (2-[4-(cyclopropanecarbonyl)phenyl]-2-methyl-propanamide)

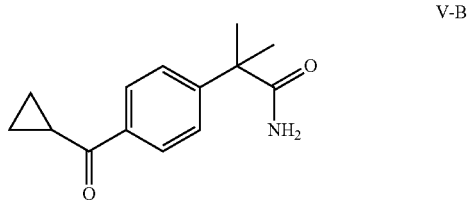 [SMILES: CC(C)(C(N)=O)c1ccc(C(=O)C2CC2)cc1]

V-B

The conversion of the nitrile into the amide can be done by methods known in the art such as by hydrolysis in an alkaline media such as described in U.S. Pat. No. 6,340,761 B1 (Example 33).

A compound of formula V, wherein R1 is an ester group COOR2, corresponds to a compound of formula V-C.

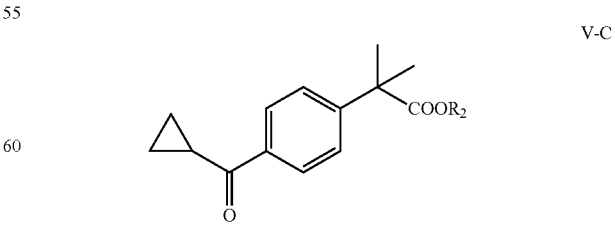

V-C wherein R2 is C1-C4 alkyl.

Such compounds are known in the art. The compound wherein R2 is methyl is described in WO 2006/034092

(AMR Technology, Ex. 1). The compound wherein R2 is ethyl is described in U.S. Pat. No. 6,340,761 (Ex. 20, Ex. 34). The compound wherein R2 is different from methyl or ethyl can be prepared in analogy to the procedure described above for the methyl or ethyl compound. Alternatively, they are readily prepared from the methyl or ethyl ester by performing a simple ester exchange known in the art (Beyer Walter, Lehrbuch der Organischen Chemie, 24 edition, Hirzel Verlag, 2004—Chapter 2.28.4.6)

Diphenyl(piperidin-4-yl)methanol (azacyclonol, CAS: 115-46-8) of formula IV is known for a long time and can be obtained according to methods described in the art such as in U.S. Pat. No. 2,804,422 (Merrel) or is commercially available from various sources such as Acros Organics or ABCR GmbH.

The reaction of the compounds of formula V and IV according to the process of the present invention is done without any solvent or optionally in the presence of a small amount of a solvent. In one embodiment of the process of the present invention for making a compound of formula II, and finally compound I, the reactants of formula V and IV are mixed together without any solvent (neat). For example, with the compound of formula V-A a yield of 69% (HPLC, AUC) of the compound of formula II-A was obtained at temperatures between 160-180° C. and a reaction time of about 7 h.

Since azacyclonol tends to sublime at reaction temperatures, optionally small amounts of solvent can be added to prevent sublimation and wash sublimed material from the dome of the reaction vessel where it would tend to collect. Thus in another embodiment of the process the reactants of formula V and azacyclonol (IV) are mixed together with small amounts of a solvent. The solvent serves primarily in facilitating the practical execution in a laboratory or plant equipment.

Solvents which can be used are aromatic solvents such as but not limited to xylene, toluene, mesitylene or polar non-protic solvents like DMF or NMP. A preferred solvent is toluene. If a solvent is added the amount of solvent is usually up to 50 wt % of the sum of the weights of compounds V and IV. In another embodiment the amount is up to 20 wt %. More preferred are up to 10 wt %, especially 1-10 wt %. For 1-10 wt % this means for instance about 10 gr to 100 gr of solvent such as toluene are added to 1 kg of a mixture of a compound of formula V and compound IV.

For a reaction of a compound of formula V with azacyclonol the reaction mixture has to be heated. The choice of the temperature depends on the desired reaction time. Lower temperatures require longer reaction times (days) while a rapid conversion is obtained at higher temperatures (minutes to hours). In one embodiment of the process of the present invention the temperature for performing the reaction is above 80° C., preferably above 100° C., more preferably above 130° C. The high temperature regime is thus well suited for continuous processing in a flow reactor.

In the embodiment, wherein R1 is COOR2 in the compounds of formula V and the product of formula II, the temperature used preferably does not exceed 150° C. since above this temperature the esters decarboxylate. Accordingly, for these compounds the temperature used is in the range of 80 to 150° C., preferably 100 to 150° C., more preferably 130 to 150° C.

In the embodiment, wherein R1 is CN or COONH2 in the compound of formula V and the product of formula II, which are more stable, higher temperatures up to 350° C. may be used. Accordingly, for these compounds the temperature used is in the range of 80 to 350° C. In one embodiment thereof a temperature in the range of 80 to 190° C. may be used. In a further embodiment 100 to 190° C. may be used. In a further embodiment 130 to 190° C., more preferably 150 to 190° C. may be used.

The reaction time depends on the nature of R1 and the temperature used and is typically in the range of several hours, such as 15 h to 24 h, whereby the amide tends to react more quickly than the nitrile. The reaction time also depends on the kind and quantity of the salt added and can be determined and adjusted by a skilled person following the description herein.

In the reaction step each of the components can be used with one equivalent or an excess, for example 1.0 to 1.2 equivalents of a compound of formula V relative to compound IV are used. For example with one equivalent of compound V-A and one equivalent of compound IV and 9 wt % of toluene stirred for 20 h at 160° C. compound II-A was obtained in about 72% yield (HPLC, AUC).

For the reaction of the ester derivatives in a compound of formula IV (R1 is COOR2) a suitable salt is added whereas this is not required for the reaction of a compound of formula IV wherein R1 is CN or CONH2. In addition to the good and surprising coupling of a compound of formula V with amine of formula IV (R1 is CN or CONH2) without adding any further reagent, it has been found that with the addition of a catalyst the conversion to the compound of formula II can be further strongly improved. A suitable catalyst is a salt derived from certain elements of the periodic system. The addition of these catalysts further improves the process and results in a faster and cleaner conversion allowing complete consumption of starting materials with reduced formation of by-products.

Thus in an embodiment of the process of the present invention the compound of formula V, wherein R1 is CN or CONH2, and the compound of formula IV are optionally reacted together in the presence of a suitable salt added to the reaction mixture. This may be done by optionally adding the salt directly to a solvent free mixture of the reactants or by adding it to the mixture in a small amount of solvent as described above. Accordingly, the following description about a suitable salt applies to the compound of formula V wherein R1 is CN, CONH2 or COOR2.

In one embodiment of the process of the present invention a salt is added wherein the salt is a salt of a chemical element selected from the first group and is a lithium (Li), sodium (Na), potassium (K), rubidium (Rb) or caesium (Cs) salt, especially a lithium (Li) or sodium (Na) salt; a salt from the second group is a magnesium (Mg), calcium (Ca), strontium (Sr) or barium (Ba) salt, especially a magnesium, calcium or barium salt; a salt from the 3d to 12th group of elements is selected from elements within the 4th period of the periodic system from scandium (Sc) to zinc (Zn), especially scandium (Sc), manganese (Mn), iron (Fe), copper (Cu) or zinc (Zn) or within the 5th period of the periodic system from yttrium (Y) to cadmium (Cd), especially silver (Ag); a salt from group thirteen is a boron (B), aluminium (Al), gallium (Ga), indium (In) or thallium (Tl) salt, especially an aluminium (Al), gallium (Ga) or indium (In) salt; a salt from the lanthanoide group is a cerium (Ce), europium (Eu), or ytterbium (Yb), or is a bismuth salt.

For the periodic system reference is made to the table of the elements according to IUPAC nomenclature, table version as of May 1, 2013; www.iupac.org.

In one embodiment the salt is a lithium, sodium, potassium, rubidium, caesium, magnesium, calcium, strontium, barium, scandium, manganese, iron, copper, zinc, silver, boron, aluminium, gallium, indium, cerium, europium, ytterbium or bismuth salt.

In another embodiment the salt is a lithium, sodium, magnesium, calcium, barium, scandium, manganese, iron, copper, silver, zinc, aluminium, gallium, indium, cerium, europium, ytterbium or bismuth salt. In another embodiment the salt is a lithium, sodium, calcium, barium, magnesium, silver, europium or iron salt. In a further embodiment the salt is a lithium, sodium, calcium or barium salt. In a further embodiment the salt is a lithium, calcium or barium salt, preferably a lithium or a barium salt, more preferably a lithium salt.

In a salt of the above mentioned elements, which salt is an ionic compound consisting of a cation and an anion, the mentioned element is the cation. The corresponding anion of the salt is chosen so that the salt has a certain solubility in the reaction medium system used for the reaction as described above. Suitable anions in the salt are chosen from halogen acids such as chloride, bromide, iodide or perchlorate, from nitric acid (nitrate), from a sulfonic acid such as trifluoromethanesulfonic acid (trifluoromethanesulfonate, also designated triflate) or from a carboxylic acid such as trifluoracetic acid (trifluoroacetate).

In one embodiment the anion in the salt is chosen from chloride, bromide, iodide, perchlorate, nitrate, trifluoromethanesulfonate or trifluoroacetate, preferably from bromide, iodide, perchlorate, nitrate, trifluoromethanesulfonate or trifluoroacetate, preferably perchlorate, trifluoromethanesulfonate or trifluoroacetate, preferably perchlorate or trifluoromethanesulfonate. In a specific embodiment the anion is perchlorate.

In one embodiment of the salts the salt is selected from lithium perchlorate, lithium trifluoromethanesulfonate, lithium bromide, lithium trifluoroacetate, lithium nitrate, lithium jodide, barium perchlorate, barium trifluoromethanesulfonate, calcium trifluoromethanesulfonate, or sodium trifluoromethanesulfonate. In a further embodiment the salt is selected from lithium perchlorate, lithium trifluoromethanesulfonate, lithium bromide, lithium trifluoroacetate, lithium nitrate, barium perchlorate, barium trifluoromethanesulfonate, or calcium trifluoromethanesulfonate. In another embodiment the salt is selected from lithium perchlorate, lithium trifluoromethanesulfonate, lithium bromide, lithium trifluoroacetate, barium perchlorate, or calcium trifluoromethanesulfonate. In yet another embodiment the salt is selected from lithium perchlorate, lithium trifluoromethanesulfonate, lithium bromide, lithium trifluoroacetate, or barium perchlorate. In a further embodiment the salt is selected from lithium perchlorate, lithium trifluoromethanesulfonate, lithium bromide, or barium perchlorate. In another embodiment the salt is selected from lithium perchlorate or barium perchlorate, In an embodiment the salt is a lithium salt. In one embodiment thereof the lithium salt is lithium chloride, lithium bromide, lithium iodide, lithium nitrate, lithium perchlorate, lithium trifluoroacetate, or lithium trifluoromethanesulfonate. In a further embodiment the lithium salt is lithium bromide, lithium nitrate, lithium trifluoroacetate, lithium trifluoromethanesulfonate or lithium perchlorate. In a further embodiment the lithium salt is lithium perchlorate (LiClO4). In another embodiment the salt is a sodium salt. In an embodiment thereof a sodium salt is sodium perchlorate or sodium trifluoromethanesulfonate. In yet another embodiment the salt is a calcium salt. In an embodiment thereof a calcium salt is calcium chloride, calcium perchlorate, or calcium trifluoromethanesulfonate.

In a further embodiment the salt is a barium salt. In an embodiment thereof the barium salt is barium perchlorate or barium trifluoromethanesulfonate. In a further embodiment the salt is a magnesium salt. In an embodiment thereof the salt is magnesium perchlorate or magnesium trifluoromethanesulfonate. In a further embodiment the salt is a scandium salt. In an embodiment thereof the salt is scandium trifluoromethanesulfonate. In a further embodiment the salt is a manganese salt. In an embodiment thereof the salt is manganese perchlorate. In a further embodiment the salt is an iron salt. In an embodiment thereof the salt is iron perchlorate. In a further embodiment the salt is a copper salt. In an embodiment thereof the salt is copper trifluoromethanesulfonate. In a further embodiment the salt is a zinc salt. In an embodiment thereof the salt is zinc perchlorate. In a further embodiment the salt is a silver salt. In an embodiment thereof the salt is silver perchlorate. In a further embodiment the salt is an aluminium salt. In an embodiment thereof the salt is aluminium perchlorate. In a further embodiment the salt is a gallium salt. In an embodiment thereof the salt is gallium perchlorate. In a further embodiment the salt is an indium salt. In an embodiment thereof the salt is indium perchlorate, indium chloride or indium trifluoromethanesulfonate. In a further embodiment the salt is a cerium salt. In an embodiment thereof the salt is cerium perchlorate or cerium trifluoromethanesulfonate. In a further embodiment the salt is a europium salt. In an embodiment thereof the salt is europium trifluoromethanesulfonate.

In a further embodiment the salt is an ytterbium salt. In an embodiment thereof the salt is ytterbium trifluoromethanesulfonate. In yet another embodiment the salt is a bismuth salt. In an embodiment thereof the salt is bismuth trifluoromethanesulfonate.

As shown in the examples the amount (equivalents) of salt added is not critical for performing the reaction. The salt is not consumed in the reaction but provides a catalytic activity which improves reaction time and/or yield. In one embodiment the amount is ranging from 0.01 to 0.5 eq. The amount used is depending on the catalytic activity of the salt. Determination of a suitable amount of a corresponding salt for performing the reaction most efficient in terms of time and other, especially economic, factors can be done by a skilled person by making corresponding experiments with said salt.

For instance a strongly improved conversion was observed with 0.01 to 0.2 mol-equivalents of LiClO4. For example, 1.2 equivalents of compound V-A, 1.0 equivalent of compound IV, 0.05 eq. of LiClO4 and 6 wt % toluene were stirred for 4 h at 150° C. The isolated yield of II-A was 91% after crystallisation from EtOH.

In a further embodiment of the process of the present invention, the compound of formula II

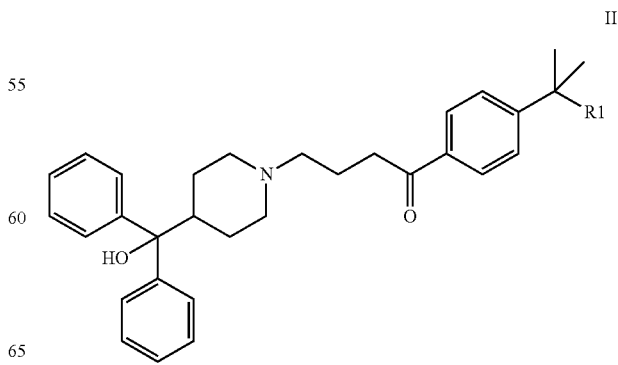

II prepared according to the various embodiments described above is further converted into a compound of formula I

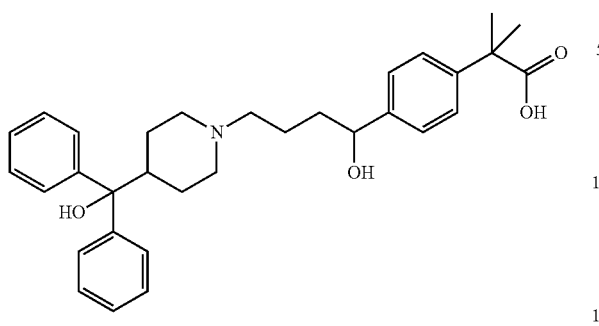

or a pharmaceutically acceptable salt thereof. The conversion of a compound of formula II into compound of formula I can be achieved in various ways. In an embodiment a compound of formula II is converted into a compound of formula I by sequentially or simultaneously reducing the ketone (to obtain the hydroxyl group) and hydrolyzing the nitrile or the amide or the ester in R1 of the compound of formula II (to obtain the carboxylic acid group).

In the embodiment of a sequential conversion, compound II (R1 is CONH2, CN or COOR2) is first reduced to obtain a compound of formula VI.

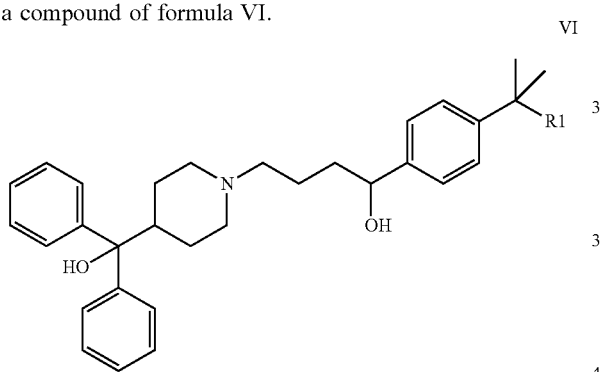

In one embodiment thereof the reduction of the ketone is done directly with a compound of formula II without prior isolation thereof after the coupling reaction of IV and V.

Accordingly, in this embodiment the compound of formula II is not isolated and directly converted into the compound of formula VI. This step is favourable if the compound of formula VI can be isolated in crystalline form.

In one embodiment of this conversion R1 is CN and the compound of formula VI-A

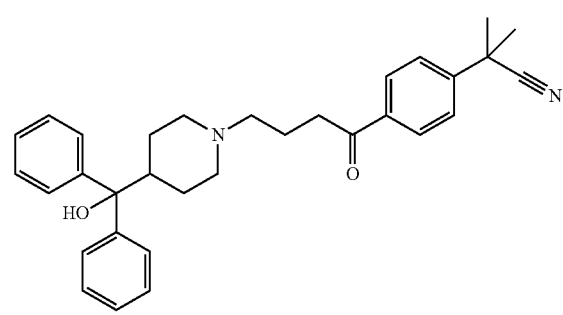

is prepared.

In another embodiment R1 is CONH2 and the compound of formula VI-B

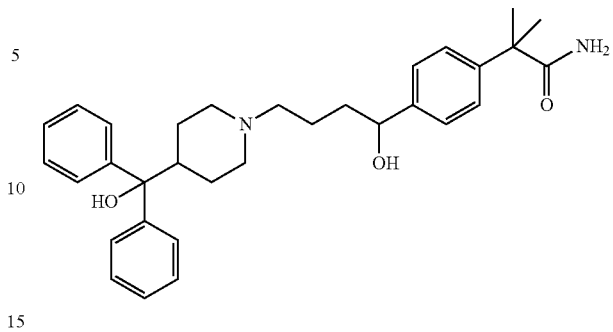

is prepared.

In another embodiment R1 is COOR2 and a compound of formula VI-C

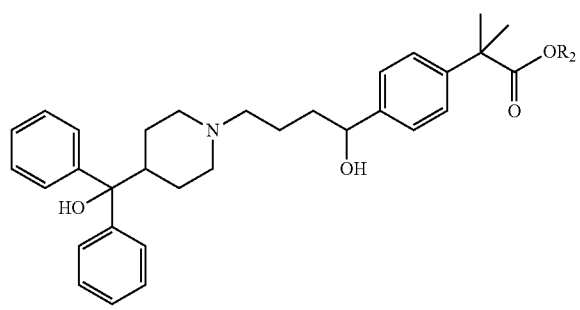

is prepared.

Reduction of the keto group in a compound of formula II wherein R1 is CN or CONH2 or COOR2, can be done by using a suitable reducing agent such as sodium borohydride, potassium borohydride, sodium cyanoborohydride, or tetramethylammonium borohydride. It is carried out in the presence of lower alcohol solvents, such as, methanol, ethanol, isopropyl alcohol, or n-butanol or mixtures of such alcohols with aromatic solvents such as toluol, optionally in the presence of some water, at temperatures ranging from about 0° C. to the reflux temperature of the solvent, and the reaction time varies from about 30 min to 8 hours. Other suitable reducing agents are, for example, lithium tri-tert-butoxylaluminum hydride and diisobutylaluminum hydride. These reduction reactions are carried out in suitable solvents such as an ether, such as diethyl ether, tetrahydrofurane or dioxane, or an aromatic hydrocarbon, such as toluene, xylene, or benzene, at temperatures ranging from about 0° C. to the reflux temperature of the solvent, and the reaction time varies from about 30 min to 8 hours.

Catalytic reduction may also be employed in the preparation of a compound of formula II, wherein R1 is CN or CONH2 or COOR2, using hydrogen gas in the presence of a suitable homogeneous or heterogeneous catalyst such as Raney nickel, or palladium, platinum or rhodium based catalysts in lower alcohol solvents, such as, methanol, ethanol, isopropyl alcohol or n-butanol or acetic acid or their aqueous mixtures, or by the use of aluminum isopropoxide in isopropyl alcohol.

As an example a compound of formula V-B and the amine of formula IV and 5 wt % mesitylene were stirred 16 h at 175° C. to yield 80% of II-B by HPLC. After cooling and without isolation the compound II-B was reduced with sodium borohydride in butanol/MeOH/water to yield 70% of compound VI-B after crystallization.

In the next step the compound of formula VI can be converted into a compound of formula I by hydrolyzing the CN or amide group or ester group to obtain the free acid. The hydrolysis can be done by known methods such as acid or base hydrolysis. For example, hydrolysis of the amide functionality may be achieved by using a suitable base, such as sodium hydroxide in methanol as known in the art. The nitrile functionality of the compound of structure VI-A is also converted to the corresponding carboxy group to give the compound of formula I. For example, hydrolysis may be achieved by using a suitable acid, such as concentrated hydrochloric acid as known in the art. The ester functionality can be converted into the acid by simple hydrolysis, preferably under basic conditions.

Alternatively, the hydrolysis of the nitrile or the amide or the ester in R1 may also be done in the first step by the methods described above to give a compound of formula VII

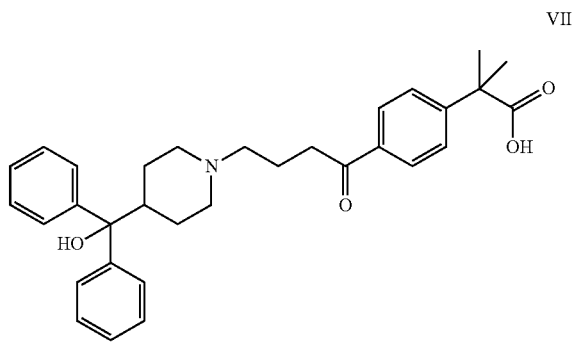 [SMILES: CC(C)(C(=O)O)c1ccc(C(=O)CCCN2CCC(C(O)(c3ccccc3)c3ccccc3)CC2)cc1]

followed by the reduction of the ketone to the hydroxy group according to the methods described above to yield a compound of formula I.

In another embodiment of the process of the present invention the compound of formula II, wherein R1 is CONH2 or CN or COOR2, is converted into the compound of formula I by simultaneously reducing the ketone and hydrolyzing the nitrile or the amide or the ester.

This can be done e.g. by using the reagent mixture KOH/sodium borohydride as described by Wang et al. (Org. Proc. Res. and Dev. 2010, 14, 1464-68). In a further embodiment the direct conversion can be done by performing reduction and hydrolysis simultaneously with the same reagent. The reduction of ketones to secondary alcohols was described by Zuidema (Synth. Comm. 2010, 1187) by using sodium hydroxide and isopropanol. It has been found that this kind of reagent can be used very efficiently for simultaneously performing the reduction of the ketone and the hydrolysis of the nitrile or the amide or the ester. Accordingly, in this embodiment the reduction/hydrolysis can be done with a base, such as sodium- or potassium hydroxide, in an alcoholic solvent, preferably a secondary alcohol such as isopropanol or isobutanol. For example one equivalent of compound II-A and two equivalents sodium hydroxide were heated for 8 h at 100° C. and 20 h at 130° C. in 2-butanol/MeOH to yield the crude sodium salt of the compound of formula I in 97% purity by HPLC.

In another embodiment of the process of the present invention the compound of formula II and any further intermediates, such as VI or VII, may not be isolated and directly converted into the compound of formula I by the various embodiments described hereinbefore.

In one embodiment the compound of formula I may be isolated as free base and free acid by adjusting the pH of the solution accordingly. In another embodiment the compound of formula I is converted into a pharmaceutically acceptable salt. The pharmaceutically acceptable acid addition salts are formed with any suitable inorganic or organic acid. Suitable inorganic acids are, for example, hydrochloric, hydrobromic, sulfuric, and phosphoric acids. Suitable organic acids include carboxylic acids, such as, acetic or propionic acid, Salts of the compound of formula I formed with inorganic or organic bases are also possible and include, for example, those of alkali metals, such as, sodium, potassium and lithium, or alkaline earth metals, for example, calcium and magnesium.

The salts are prepared by conventional means as, for example, by treating a compound of formula I with an appropriate acid or base. In one embodiment the hydrochloride (HCl) salt of a compound of formula I is prepared.

ABBREVIATIONS

° C. degree Celsius
AcOEt ethyl acetate
AUC area under curve
Bu butyl
BuOH butanol
ca. circa
d dublett
DIPA Diisopropylamine
DMF Dimethylformamide
Et ethyl
Eq. Equivalents
h hour(s)
HPLC high performance liquid chromatography
LC-MS liquid chromatography-mass spectrometry
m multiplet
Me methyl
min minutes
NMR Nuclear magnetic resonance
rt room temperature
$R_t$ retention time
s singulett
THF tetrahydrofuran
TMS tetramethylsilane

EXAMPLES

The invention is described in more detail by the following examples. These examples are designated to illustrate the invention, but do not limit its scope. Each step of the process described in the present invention is scalable on larger amounts than described here.

The NMR assignments are for illustration only based on analysis of the one-dimensional $^1$H NMR spectra as done by those skilled in the art. A more detailed analysis of the spectra may lead to minor reassignments of some NMR peaks, which obviously does not change the overall assignment. All $^1$H NMR spectra are recorded on a 500 MHz instrument at rt. Shifts are relative to TMS in [ppm]; the solvent is always DMSO-$d_6$.

Reference Example 1

Reaction of azacyclonol (Diphenyl(piperidin-4-yl)methanol, CAS: 115-46-8) (IV) with 2-[4-(cyclopropanecarbonyl-)-phenyl]-2-methyl-propanenitrile according to the coupling conditions described in Table 2 of Wang et al. (Org. Proc. Res. and Dev. 2010, 14, 1464-68).

The table depicted below lists the reaction conditions (solvent, base, temperature) set forth in Table 2 of Wang et al. for reacting azacyclonol with a compound of formula III (X is Br, Cl, OTs; R1 is nitril) to obtain a compound of formula II-A and, as side product, a compound of formula V-A. If this nitrile by-product V-A is tested under the reaction conditions mentioned by Wang it does not react with azacyclonol to compound II-A as described below for each entry in more detail.

| Entry | solvent | base | T (° C.) | yield II-A (%)* |
|-------|---------|------|----------|-----------------|
| 1 | THF | $Na_2CO_3$ | 60 | 0 |
| 2 | THF | $NaHCO_3$ | 60 | 0 |
| 3 | DMF | $Et_3N$ | 25 | 0 |
| 4 | THF | $Et_3N$ | 25 | 0 |
| 5 | THF | DIPA | 25 | 0 |
| 6 | acetone | $NaHCO_3$ | 60 | 0 |
| 7 | acetone | $Et_3N$ | 60 | 0 |

*The detection limit was 0.1 mol %

Entry 1

2-[4-(cyclopropanecarbonyl-)-phenyl]-2-methyl-propanenitrile of formula V-A (2.13 g, 10.0 mmol) were dissolved in 9.4 ml THF, Azacyclonol (3.21 g, 12.0 mmol, 1.2 eq.) and $Na_2CO_3$ (1.06 g; 10.0 mmol; 1.0 eq.) were added before stirring the mixture at 60° C. for 8 hours.

The assay was performed by diluting an aliquot taken from the reaction mixture in the standard manner.

HPLC (AUC, Merck Chromolith Performance RP18e, A: $H_2O$/0.05% TFA, B: MeCN/0.05% TFA, 20->70% B in 7 min, 4 ml/min, 40° C., UV: 210 nm): $R_t$ (Standard II-A)=3.57 min Product II-A was not detectable. Addition of an aliquot corresponding to 0.1% of II-A to the diluted reaction mixture leads to a detectable peak, showing that less than 0.1% were formed in the reaction.

Entry 2

2-[4-(cyclopropanecarbonyl-)-phenyl]-2-methyl-propanenitrile of formula V-A (2.13 g, 10.0 mmol) were dissolved in 9.4 ml THF, Azacyclonol (3.21 g, 12.0 mmol, 1.2 eq.) and $NaHCO_3$ (0.84 g; 10.0 mmol; 1.0 eq.) were added before stirring the mixture at 60° C. for 8 hours.

HPLC (AUC, Merck Chromolith Performance RP18e, A: $H_2O$/0.05% TFA, B: MeCN/0.05% TFA, 20->70% B in 7 min, 4 ml/min, 40° C., UV: 210 nm): $R_t$ (Standard II-A)=3.57 min Product II-A was not detectable. Addition of an aliquot corresponding to 0.1% of II-A to the diluted reaction mixture leads to a detectable peak, showing that less than 0.1% were formed in the reaction Entry 3

2-[4-(cyclopropanecarbonyl-)-phenyl]-2-methyl-propanenitrile of formula V-A (2.13 g, 10.0 mmol) were dissolved in 9.4 ml DMF. Azacyclonol (3.21 g, 12.0 mmol, 1.2 eq.) and $NEt_3$ (1.39 ml; 10.0 mmol; 1.0 eq) were added before stirring the mixture at 25° C. for 8 hours.

HPLC (AUC, Merck Chromolith Performance RP18e, A: $H_2O$/0.05% TFA, B: MeCN/0.05% TFA, 20->70% B in 7 min, 4 ml/min, 40° C., UV: 210 nm): $R_t$ (Standard II-A)=3.55 min Product II-A was not detectable. Addition of an aliquot corresponding to 0.1% of II-A to the diluted reaction mixture leads to a detectable peak, showing that less than 0.1% were formed in the reaction Entry 4

2-[4-(cyclopropanecarbonyl-)-phenyl]-2-methyl-propanenitrile of formula V-A (2.13 g, 10.0 mmol) were dissolved in 9.4 ml THF. Azacyclonol (3.21 g, 12.0 mmol, 1.2 eq.) and $NEt_3$ (1.39 ml; 10.0 mmol; 1.0 eq.) were added before stirring the mixture at 25° C. for 8 hours.

HPLC (AUC, Merck Chromolith Performance RP18e, A: $H_2O$/0.05% TFA, B: MeCN/0.05% TFA, 20->70% B in 7 min, 4 ml/min, 40° C., UV: 210 nm): $R_t$ (Standard II-A)=3.56 min Product II-A was not detectable. Addition of an aliquot corresponding to 0.1% of II-A to the diluted reaction mixture leads to a detectable peak, showing that less than 0.1% were formed in the reaction Entry 5

2-[4-(cyclopropanecarbonyl-)-phenyl]-2-methyl-propanenitrile of formula V-A (2.13 g, 10.0 mmol) were dissolved in 9.4 ml THF. Azacyclonol (3.21 g, 12.0 mmol, 1.2 eq.) and DIPA (1.4 ml; 10.0 mmol; 1.0 eq.) were added before stirring the mixture at 25° C. for 8 hours.

HPLC (AUC, Merck Chromolith Performance RP18e, A: $H_2O$/0.05% TFA, B: MeCN/0.05% TFA, 20->70% B in 7 min, 4 ml/min, 40° C., UV: 210 nm): $R_t$ (Standard II-A)=3.61 min Product II-A was not detectable. Addition of an aliquot corresponding to 0.1% of II-A to the diluted reaction mixture leads to a detectable peak, showing that less than 0.1% were formed in the reaction Entry 6

2-[4-(cyclopropanecarbonyl-)-phenyl]-2-methyl-propanenitrile of formula V-A (2.13 g, 10.0 mmol) were dissolved in 9.4 ml acetone. Azacyclonol (3.21 g, 12.0 mmol, 1.2 eq.) and $NaHCO_3$ (0.84 g; 10.0 mmol; 1.0 eq.) were added before stirring the mixture at 55° C. for 8 hours.

HPLC (AUC, Merck Chromolith Performance RP18e, A: $H_2O$/0.05% TFA, B: MeCN/0.05% TFA, 20->70% B in 7 min, 4 ml/min, 40° C., UV: 210 nm): $R_t$ (Standard II-A)=3.61 min Product II-A was not detectable. Addition of an aliquot corresponding to 0.1% of II-A to the diluted reaction mixture leads to a detectable peak, showing that less than 0.1% were formed in the reaction Entry 7

2-[4-(cyclopropanecarbonyl-)-phenyl]-2-methyl-propanenitrile of formula V-A (2.13 g, 10.0 mmol) were dissolved in 9.4 ml acetone. Azacyclonol (3.21 g, 12.0 mmol, 1.2 eq.) and $NEt_3$ (1.39 ml; 10.0 mmol; 1.0 eq.) were added before stirring the mixture at 55° C. for 8 hours.

HPLC (AUC, Merck Chromolith Performance RP18e, A: $H_2O$/0.05% TFA, B: MeCN/0.05% TFA, 20->70% B in 7 min, 4 ml/min, 40° C., UV: 210 nm): $R_t$ (Standard II-A)=3.61 min Product II-A was not detectable. Addition of an aliquot corresponding to 0.1% of II-A to the diluted reaction mixture leads to a detectable peak, showing that less than 0.1% were formed in the reaction.

Reference Example 2

Reaction of azacyclonol (Diphenyl(piperidin-4-yl)methanol, CAS: 115-46-8) (IV) with 2-[4-(cyclopropanecarbonyl-)-phenyl]-2-methyl-propanenitrile (V-A) according to coupling conditions described by Yovell et al. (J. Org. Chem. 42, 850-855, 1977, page 855) to obtain a compound of formula II-A (as indicated in WO2006/034092/AMR Techn.).

a) Reaction According to Yovell

2-[4-(cyclopropanecarbonyl-)-phenyl]-2-methyl-propanenitrile of formula V-A (1.07 g, 5.0 mmol) and azacyclonol (1.34 g, 5.0 mmol, 1.0 eq.) and 2.4 ml o-xylene were added to a 25 ml 3-neck flask. p-Toluenesulfonic acid monohydrate (95 mg, 0.5 mmol 0.1 eq, CAS: 6192-52-5) were added and the mixture was heated to reflux (bath temperature about 150° C.).

Monitoring the reaction by HPLC showed about 7% product II-A after 2 hours and about 46% after 20 hours.

HPLC (AUC, Merck Chromolith Performance RP18e, A: H$_2$O/0.05% TFA, B: MeCN/0.05% TFA, 10->70% B in 7 min, 4 ml/min, 40° C., UV: 210 nm Rt=4.11 min b) Use of an Increased Amount of pTsOH 2-[4-(cyclopropanecarbonyl-)-phenyl]-2-methyl-propanenitrile of formula V-A (1.07 g, 5.0 mmol) and azacyclonol (1.34 g, 5.0 mmol, 1.0 eq.) and 2.4 ml o-xylene were added to a 25 ml 3-neck-flask. P-Toluenesulfonic acid monohydrate (950 mg, 5.0 mmol, 1 eq, CAS: 6192-52-5) were added and the mixture was heated to reflux (bath temperature about 150° C.).

Conversion was monitored by HPLC and LC-MS (vide infra).

II-A can be detected only in small trace amounts.

The major product with 49% (by HPLC) is by HPLC comparison with authentic material and LC-MS 4-(Diphenylmethylene)piperidine (CAS: 50706-57-5), resulting from elimination of water from the tertiary alcohol.

HPLC (AUC, Merck Chromolith Performance RP18e, A: H$_2$O+0.05% TFA, B: MeCN/0.05% TFA, 10->70% B in 7 min, 4 ml/min, 40° C., UV: 210 nm) Rt=3.14 min LC-MS: (YMC J' sphere ODS H 80×20×2.1 mm, 4 µm, A: H$_2$O+ 0.05% TFA, B: MeCN, 4%->95% B in 2 min., 1 ml/min, 30° C., UV: 220 nm; MS: ESI) Rt=1.21 min, MH$^+$ 250.

Example 1

Catalyst evaluation based on a general procedure for preparing 2-[4-[4-[4-[hydroxy(diphenyl)methyl]-1-piperidyl]butanoyl]phenyl]-2-methyl-propanenitrile (480.7 g/mol) of formula II-A using azacyclonol (Diphenyl(piperidin-4-yl)methanol, CAS: 115-46-8) of formula IV, 2-[4-(cyclopropanecarbonyl-)-phenyl]-2-methyl-propanenitrile of formula V-A and different salts as catalysts, partly additionally a salt with different amounts:

Azacyclonol (2.67 g, 10.0 mmol) and 2-[4-(cyclopropanecarbonyl-)-phenyl]-2-methyl-propanenitrile of formula V-A (2.13 g, 10 mmol) were placed in 25 ml 3-neeked flask. Toluene (0.3 ml, 5 wt %) and the catalyst as specified below in the single experiments were added and the mixture was heated to 150° C. and stirred for 20 h. Conversion was followed by HPLC and LC-MS (vide infra). Samples were taken at 150° C. after 2 h and 20 h. HPLC (AUC, Merck Chromolith Performance RP18e, A. H$_2$O/0.05% TFA, B: MeCN/0.05% TFA, 10->70% B in 7 min, 4 ml/min, 40° C., UV: 210 nm).

Isolation: The mixture was cooled to 110° C., EtOH (17 ml) was added carefully and the mixture was allowed cooling down to rt with stirring. The solid was filtered and the filter cake was washed with cold EtOH to yield the title compound II-A as a white solid. The products were characterised by HPLC (vide supra) and LC-MS: (YMC J' sphere ODS H 80 20×2.1 mm, 4 µm, A: H$_2$O+0.05% TFA, B: MeCN, 4%→95% B in 2 min, 1 ml/min, 30° C., UV: 220 nm; MS: ESI).

Example A

Example a1

Reaction was performed as described in the general procedure without any catalyst (reference example). The yield after 2 hours was 18% (by HPLC) and 62% after 20 hours (by HPLC) and the title compound was finally isolated (2.55 g, 53%) according to the general procedure. In short the determination of the yield via HPLC is summarized as follows and this description is also used in the following examples:

HPLC (2 h): 18% product yield (AUC); HPLC (20 h): 62% product yield (AUC), R$_t$=4.20 min; LC-MS: R$_t$=1.22 min, MH$^+$ 481.

Example a2

0.21 g (5.0 mmol, 0.5 equivalents) Lithium chloride (CAS: 7447-41-8) from Sigma Aldrich was used as described in the general procedure to yield 3.42 g (71%) of the title compound. HPLC (2 h): 38% product yield (AUC); HPLC (20 h): 77% product yield (AUC), R$_t$=4.18 min; LC-MS: R$_t$=1.22 min, MH$^+$ 481.

Example a3

85 mg (2.0 mmol, 0.2 equivalents) Lithium chloride (CAS: 7447-41-8) from Sigma Aldrich were used as described in the general procedure to yield 3.32 g (69%) of the title compound. HPLC (2 h): 36% product yield (AUC); HPLC (20 h): 76% product yield (AUC), R$_t$=4.19 min; LC-MS: R$_t$=1.21 min, MH$^+$ 481.

Example a4

42 mg (1.0 mmol, 0.1 equivalents) Lithium chloride (CAS: 7447-41-8) from Sigma Aldrich were used as described in the general procedure to yield 2.99 g (62%) of the title compound. HPLC (2 h): 33% product yield (AUC); HPLC (20 h): 71% product yield (AUC), R$_t$=4.20 min; LC-MS: R$_t$=1.22 min, MH$^+$ 481.

Example a5

0.21 g (5.0 mmol, 0.5 equivalents) Lithium chloride (CAS: 7447-41-8) from Sigma Aldrich was used as described in the general procedure to yield 3.04 g (63%) of the title compound using MIBK as solvent. HPLC (2 h): 29% product yield (AUC); HPLC (20 h): 68% product yield (AUC), R$_t$=4.21 min; LC-MS: R$_t$=1.22 min, MH$^+$ 481.

Example a6

0.60 g (5.0 mmol, 0.5 equivalents) Lithium trifluoroacetate (CAS: 2923-17-3) from Sigma Aldrich was used as described in the general procedure to yield 3.76 g (78%) of the title compound. HPLC (2 h): 77% product yield (AUC); HPLC (20 h): 91% product yield (AUC), R$_t$=4.17 min; LC-MS: R$_t$=1.21 min, MH$^+$ 481.

Example a7

0.24 g (2.0 mmol, 0.2 equivalents) Lithium trifluoroacetate (CAS: 2923-17-3) from Sigma Aldrich were used as described in the general procedure to yield 3.92 g (82%) of the title compound. HPLC (2 h): 70% product yield (AUC);

HPLC (20 h): 91% product yield (AUC), $R_f$=4.22 min; LC-MS: $R_t$=1.22 min, MH$^+$ 481.

Example a8

0.34 g (5.0 mmol, 0.5 equivalents) Lithium nitrate (CAS: 7790-69-4) from Sigma Aldrich was used as described in the general procedure to yield 3.66 g (76%) of the title compound. HPLC (2 h): 55% product yield (AUC), HPLC (20 h): 84% product yield (AUC), $R_f$=4.22 min; LC-MS: $R_t$=1.21 min, MH$^+$ 481.

Example a9

0.56 g (5.0 mmol, 0.5 equivalents) Calcium chloride (CAS: 10043-52-4) from Fisher Scientific was used as described in the general procedure to yield 3.10 g (65%) of the title compound. HPLC (2 h): 30% product yield (AUC); HPLC (20 h): 73% product yield (AUC), $R_f$=4.22 min; LC-MS: $R_t$=1.23 min, MH$^+$ 481.

Example a10

21 mg (0.2 mmol, 0.02 equivalents) Lithium perchlorate (CAS: 7791-03-9) from Sigma Aldrich were used as described in the general procedure without isolation of the title compound. HPLC (2 h): 57% product yield (AUC); HPLC (20 h): 84% product yield (AUC), $R_f$=4.22 min; LC-MS: $R_t$=1.21 min, MH$^+$ 481.

Example B

In the following examples the experiment as described in the general procedure was slightly modified by fixing the amount of catalyst and performing yield measurement after 2 hours only: 5.00 mmol of compound IV (1.34 g), 5.00 mmol of compound V-A (1.07 g) and a constant amount of 0.2 equivalents (1.0 mmol) of the mentioned catalyst and 0.1 ml (3 wt %) Toluol were used. The conversion was measured only after 2 h stirring at 150° C. and the product was not isolated. The yield increase over time as shown in the examples above does not require to perform the reaction until the end. The reference value for the conversion after 2 hours is the conversion measured in example (a1) above after 2 hours (18%).

Example b1

106 mg (1.00 mmol, 0.2 equivalents) Lithium perchlorate (CAS: 7791-03-9) from Acros was used as described in the modified general procedure. HPLC (2 h): 82% product yield (AUC), $R_f$=4.27 min; LC-MS: $R_t$=1.22 min, MH$^+$ 481.

Example b2

120 mg (1.00 mmol, 0.2 equivalents) Lithium triflate (CAS: 33454-82-9) from Sigma Aldrich was used as described in the modified general procedure. HPLC (2 h): 90% product yield (AUC), $R_f$=4.27 min; LC-MS: $R_t$=1.22 min, MH$^+$ 481.

Example b3

87 mg (1.00 mmol, 0.2 equivalents) Lithium bromide (CAS: 7550-35-8) from Sigma Aldrich was used as described in the modified general procedure. HPLC (2 h): 80% product yield (AUC), $R_f$=4.27 min; LC-MS: $R_t$=1.21 min, MH$^+$ 481.

Example b4

134 mg (1.00 mmol, 0.2 equivalents) Lithium iodide (CAS: 10377-51-2) from Acros was used as described in the modified general procedure. HPLC (2 h): 40% product yield (AUC), $R_f$=4.32 min; LC-MS: $R_t$=1.22 min, MH$^+$ 481.

Example b5

172 mg (1.00 mmol, 0.2 equivalents) Sodium triflate (CAS: 2926-30-9) from Acros was used as described in the modified general procedure. HPLC (2 h): 48% product yield (AUC), $R_f$=4.15 min; LC-MS: $R_t$=1.23 min, MH$^+$ 481.

Example b6

122 mg (1.00 mmol, 0.2 equivalents) Sodium perchlorate (CAS: 7601-89-0) from Sigma Aldrich was used as described in the modified general procedure. HPLC (2 h): 28% product yield (AUC), $R_f$=4.16 min; LC-MS: $R_t$=1.23 min, MH$^+$ 481.

Example b7

136 mg (1.00 mmol, 0.2 equivalents) Sodium trifluoroacetate (CAS: 2923-18-4) from Sigma Aldrich was used as described in the modified general procedure.
HPLC (2 h): 32% product yield (AUC), $R_f$=4.16 min; LC-MS: $R_t$=1.25 min, MH$^+$ 481.

Example b8

150 mg (1.00 mmol, 0.2 equivalents) Sodium iodide (CAS: 7681-82-5) from Sigma Aldrich was used as described in the modified general procedure. HPLC (2 h): 33% product yield (AUC), $R_f$=4.19 min; LC-MS: $R_t$=1.24 min, MH$^+$ 481.

Example b9

322 mg (1.00 mmol, 0.2 equivalents) Magnesium triflate (CAS: 10377-51-2) from Acros was used as described in the modified general procedure. HPLC (2 h): 67% product yield (AUC), $R_f$=4.31 min; LC-MS: $R_t$=1.22 min, MH$^+$ 481.

Example b10

223 mg (1.00 mmol, 0.2 equivalents) Magnesium perchlorate (CAS: 10034-81-8) from Sigma Aldrich was used as described in the modified general procedure. HPLC (2 h): 55% product yield (AUC), $R_f$=4.15 min; LC-MS: $R_t$=1.24 min, MH$^+$ 481.

Example b11

311 mg (1.00 mmol, 0.2 equivalents) Calcium perchlorate tetra hydrate (CAS: 15627-86-8) from Acros was used as described in the modified general procedure. HPLC (2 h): 38% product yield (AUC), $R_f$=4.29 min; LC-MS: $R_t$=1.21 min, MH$^+$ 481.

Example b12

336 mg (1.00 mmol, 0.2 equivalents) Barium perchlorate (CAS: 13465-95-7) from ABCR was used as described in the modified general procedure. HPLC (2 h): 87% product yield (AUC), $R_t$=4.14 min; LC-MS: $R_t$=1.23 min, MH$^+$ 481.

Example b13

436 mg (1.00 mmol, 0.2 equivalents) Barium triflate (CAS: 2794-60-7) from ABCR was used as described in the modified general procedure. HPLC (2 h): 52% product yield (AUC), $R_t$=4.16 min; LC-MS: $R_t$=1.22 min, MH$^+$ 481.

Example b14

487 mg (1.00 mmol, 0.2 equivalents) Aluminium perchlorate nonahydrate (CAS: 81029-06-3) from ABCR was used as described in the modified general procedure. HPLC (2 h): 28% product yield (AUC), $R_t$=4.18 min; LC-MS: $R_t$=1.24 min, MH$^+$ 481.

Example b15

368 mg (1.00 mmol, 0.2 equivalents) Gallium perchlorate hydrate (CAS: 81029-07-4) from Sigma Aldrich was used as described in the modified general procedure. HPLC (2 h): 29% product yield (AUC), $R_t$=4.19 min; LC-MS: $R_t$=1.25 min, MH$^+$ 481.

Example b16

413 mg (1.00 mmol, 0.2 equivalents) Indium perchlorate hydrate (CAS: 314041-16-2) from Sigma Aldrich was used as described in the modified general procedure. HPLC (2 h): 38% product yield (AUC), $R_t$=4.18 min; LC-MS: $R_t$=1.23 min, MH$^+$ 481.

Example b17

221 mg (1.00 mmol, 0.2 equivalents) Indium chloride (CAS: 10025-82-8) from Strem Chemicals was used as described in the modified general procedure. HPLC (2 h): 29% product yield (AUC), $R_t$=4.19 min; LC-MS: $R_t$=1.22 min, MH$^+$ 481.

Example b18

562 mg (1.00 mmol, 0.2 equivalents) Indium triflate (CAS: 128008-30-0) from Strem Chemicals was used as described in the modified general procedure. HPLC (2 h): 38% product yield (AUC), $R_t$=4.17 min; LC-MS: $R_t$=1.23 min, MH$^+$ 481.

Example b19

492 mg (1.00 mmol, 0.2 equivalents) Scandium triflate (CAS: 144026-79-9) from Sigma Aldrich was used as described in the modified general procedure. HPLC (2 h): 53% product yield (AUC), $R_t$=4.18 min; LC-MS: $R_t$=1.22 min, MH$^+$ 481.

Example b20

620 mg (1.00 mmol, 0.2 equivalents) Ytterbium triflate (CAS: 54761-04-5) from Sigma Aldrich was used as described in the modified general procedure. HPLC (2 h): 56% product yield (AUC), $R_t$=4.18 min; LC-MS: $R_t$=1.22 min, MH$^+$ 481.

Example b21

225 mg (1.00 mmol, 0.2 equivalents) Silver perchlorate (CAS: 14242-05-8) from ABCR was used as described in the modified general procedure. HPLC (2 h): 48% product yield (AUC), $R_t$=4.18 min; LC-MS: $R_t$=1.23 min, MH$^+$ 481.

Example b22

254 mg (1.00 mmol, 0.2 equivalents) Manganese(II) perchlorate hydrate (CAS: 698999-57-4) from Sigma Aldrich was used as described in the modified general procedure. HPLC (2 h): 42% product yield (AUC), $R_t$=4.19 min; LC-MS: $R_t$=1.24 min, MH$^+$ 481.

Example b23

255 mg (1.00 mmol, 0.2 equivalents) Iron(II) perchlorate hydrate (CAS: 335159-18-7) from Sigma Aldrich was used as described in the modified general procedure. HPLC (2 h): 41% product yield (AUC), $R_t$=4.20 min; LC-MS: $R_t$=1.24 min, MH$^+$ 481.

Example b24

354 mg (1.00 mmol, 0.2 equivalents) Iron(III) perchlorate hexahydrate (CAS: 15201-61-3) from Sigma Aldrich was used as described in the modified general procedure. HPLC (2 h): 35% product yield (AUC), $R_t$=4.20 min; LC-MS: $R_t$=1.24 min, MH$^+$ 481.

Example b25

362 mg (1.00 mmol, 0.2 equivalents) Copper(II) triflate (CAS: 34946-82-2) from Fluka was used as described in the modified general procedure. HPLC (2 h): 41% product yield (AUC), $R_t$=4.19 min; LC-MS: $R_t$=1.23 min, MH$^+$ 481.

Example b26

372 mg (1.00 mmol, 0.2 equivalents) Zinc perchlorate hexahydrate (CAS: 10025-64-6) from ABCR was used as described in the modified general procedure.
HPLC (2 h): 35% product yield (AUC), $R_t$=4.18 min; LC-MS: $R_t$=1.25 min, MH$^+$ 481.

Example b27

550 mg (1.00 mmol, 0.2 equivalents) Cerium(III) perchlorate hexahydrate (CAS: 14017-47-1) from Alfa Aesar was used as described in the modified general procedure. HPLC (2 h): 29% product yield (AUC), $R_t$=4.19 min; LC-MS: $R_t$=1.24 min, MH$^+$ 481.

Example b28

590 mg (1.00 mmol, 0.2 equivalents) Cerium(III) triflate (CAS: 76089-77-55) from ABCR was used as described in the modified general procedure. HPLC (2 h): 56% product yield (AUC), $R_t$=4.18 min; LC-MS: $R_t$=1.23 min, MH$^+$ 481.

Example b29

600 mg (1.00 mmol, 0.2 equivalents) Europium(III) triflate (CAS: 52093-25-1) from ABCR was used as described in the modified general procedure. HPLC (2 h): 69% product yield (AUC), $R_t$=4.17 min; LC-MS: $R_t$=1.23 min, MH$^+$ 481.

Example b30

656 mg (1.00 mmol, 0.2 equivalents) Bismuth triflate (CAS: 88189-03-1) from Sigma Aldrich was used as described in the modified general procedure. HPLC (2 h): 42% product yield (AUC), $R_t$=4.18 min; LC-MS: $R_t$=1.24 min, MH$^+$ 481.

Example 2

2-[4-[4-[4-[hydroxy(diphenyl)methyl]-1-piperidyl]butanoyl]phenyl]-2-methyl-propanenitrile of Formula II-A Using Lithium Perchlorate as Catalyst Azacyclonol (10.8 g, 40.0 mmol), 2-[4-(cyclopropanecarbonyl-)-phenyl]-2-methyl-propanenitrile of formula V-A (10.2 g, 48.0 mmol, 1.2 eq.) and LiClO4 (213 mg, 2.00 mmol, 0.05 eq.) and 1.5 ml (6 wt %) toluene were stirred for 4 h at 150° C. The mixture was cooled to 110° C., EtOH (77 ml) was added carefully and the mixture was allowed cooling done slowly to rt with stirring. The solid was filtered and the filter cake was washed cold EtOH to yield 17.5 g (36.4 mmol, 91%) of the title compound as a white solid.

HPLC (AUC, Merck Chromolith Performance RP18e, A. H$_2$O/0.05% TFA, B: MeCN/0.05% TFA, 10->70% B in 7 min, 4 ml/min, 40° C., UV: 210 nm): $R_t$=4.30 min; LC-MS: (YMC J' sphere ODS H 80 20×2.1 mm, 4 μm, A: H$_2$O+0.05% TFA, B: MeCN, 4%→95% B in 2 min, 1 ml/min, 30° C., UV: 220 nm; MS: ESI): $R_t$=1.23 min, MH$^+$ 481; NMR (400 MHz): 1.15-1.26 (m, 2H), 1.33-1.48 (m, 2H), 1.71 (s, 6H, 2×CH$_3$), 1.74 (q, 2H), 1.80-1.91 (m, 2H), 2.21-2.32 (m, 2H), 2.37-2.49 (m, 1H), 2.76-2.86 (m, 2H), 2.99 (t, 2H), 5.17 (s, 1H, OH), 7.08-7.15 (m, 2H, Ar—H), 7.21-7.28 (m, 4H, Ar—H), 7.46-7.53 (m, 4H, Ar—H), 7.62-7.68 (m, 2H, Ar—H), 7.95-8.02 (m, 2H, Ar—H); mp: 136° C. (EtOH).

Example 3

2-[4-[4-[4-[hydroxy(diphenyl)methyl]-1-piperidyl]butanoyl]phenyl]-2-methyl-propanenitrile of Formula II-A Using LiCl as Catalyst Azacyclonol (118 g, 440 mmol), 2-[4-(cyclopropanecarbonyl-)-phenyl]-2-methyl-propanenitrile of formula V-A (94.4 g, 443 mmol,) and LiCl (9.28 g, 220 mmol, 0.5 eq.) and 180 ml toluene were warmed to reflux and the solvent was distilled from the reaction mixture until the reaction temperature was 150° C. (remaining solvent about 5 ml (2 wt %). The mixture was stirred for 20 h at 150° C. The mixture was cooled to 110° C., EtOH (740 ml) was added carefully and the mixture was allowed cooling down slowly to rt with stirring. The solid was filtered and the filter cake was washed with cold EtOH to yield 157 g (327 mmol, 74%) of the title compound as a white solid.

LC-MS: (YMC J' sphere ODS H 80 20×2.1 mm, 4 μm, A: H$_2$O+0.05% TFA, B: MeCN, 4%→95% B in 2 min, 1 ml/min, 30° C., UV: 220 nm; MS: ESI): $R_t$=1.23 min, MH$^+$ 481.

Example 4

2-[4-[4-[4-[hydroxy(diphenyl)methyl]-1-piperidyl]butanoyl]phenyl]-2-methyl-propanenitrile of Formula II-A Using Li-trifluoroacetate as Catalyst Azacyclonol (21.5 g, 80.0 mmol), 2-[4-(cyclopropanecarbonyl-)-phenyl]-2-methyl-propanenitrile of formula V-A (17.9 g, 84.0 mmol, 1.05 eq.) and Lithium trifluoroacetate (0.96 g, 8.0 mmol, 0.1 eq.) and 2 ml (4 wt %) toluene were stirred for 17 h at 145° C. The mixture was cooled to 110° C., EtOH (154 ml) was added carefully and the mixture was allowed cooling down slowly to rt with stirring. The solid was filtered and the filter cake was washed with cold EtOH to yield 32.7 g (68.0 mmol, 85%) of the title compound as a white solid.

HPLC: $R_t$=4.28 min; LC-MS: (YMC J' sphere ODS H 80 20×2.1 mm, 4 μm, A: H$_2$O+0.05% TFA, B: MeCN, 4%→95% B in 2 min, 1 ml/min, 30° C., UV: 220 nm; MS: ESI): $R_t$=1.23 min, MH$^+$ 481.

Example 5

2-[4-[4-[4-[hydroxy(diphenyl)methyl]-1-piperidyl]butanoyl]phenyl]-2-methyl-propanenitrile of Formula II-A Using LiBr as Catalyst Azacyclonol (10.8 g, 40.0 mmol), 2-[4-(cyclopropanecarbonyl-)-phenyl]-2-methyl-propanenitrile of formula V-A (8.96 g, 42.0 mmol, 1.05 eq.) and LiBr (695 mg, 8.0 mmol, 0.2 eq.) and 1 ml (4 wt %) toluene were stirred for 6 h at 150° C. The mixture was cooled to 110° C., EtOH (67 ml) was added carefully and the mixture was allowed cooling down slowly to rt with stirring. The solid was filtered and the filter cake was washed with cold EtOH to yield 16.6 g (34.5 mmol, 86%) of the title compound as a white solid.

HPLC: $R_t$=4.27 min; LC-MS: (YMC J' sphere ODS H 80 20×2.1 mm, 4 μm, A: H$_2$O+0.05% TFA, B: MeCN, 4%→95% B in 2 min, 1 ml/min, 30° C., UV: 220 nm; MS: ESI): $R_t$=1.23 min, MH$^+$ 481.

Example 6a

2-[4-[4-[4-[hydroxy(diphenyl)-methyl]-1-piperidyl]butanoyl]phenyl]-2-methyl-Propanamide of the Formula II-B without any Catalyst and Solvent 500 mg (2.16 mmol, 1.2 eq.) 2-[4-(cyclopropanecarbonyl)phenyl]-2-methyl-propanamide of formula V-B and 480 mg (1.80 mmol, 1.0 eq.) azacyclonol were stirred for 7 h at 175° C. Analysis by HPLC revealed the formation of 69% of title compound among with unreacted starting materials. HPLC (AUC, Merck Chromolith Performance RP18e, A. H$_2$O/0.05% TFA, B: MeCN/0.05% TFA, 10->70% B in 7 min, 4 ml/min, 40° C., UV: 210 nm): $R_t$=3.18 min; LC-MS: (YMC J' sphere ODS H 80 20×2.1 mm, 4 μm, A: H$_2$O+0.05% TFA, B: MeCN, 4%→95% B in 2 min, 1 ml/min, 30° C., UV: 220 nm; MS: ESI): $R_t$=1.09 min, MH$^+$ 499.

Example 6b

2-[4-[4-[4-[hydroxy(diphenyl)-methyl]-1-piperidyl]butanoyl]phenyl]-2-methyl-propanamide of the Formula II-B with CaCl$_2$) as Catalyst 1.00 g (4.33 mmol, 1.05 eq.) 2-[4-(cyclopropanecarbonyl)phenyl]-2-methyl-propanamide of formula V-B and 1.10 g (4.12 mmol, 1.0 eq.) azacyclonol and Calcium chloride (46 mg, 0.41 mmol, 0.1 eq.) were stirred in 0.2 ml (8 wt %) p-xylene for 11 h at 145° C. p-Xylene (8 ml) was added, the mixture was refluxed shortly and was then filtered after cooling to rt to yield 1.50 g (3.00 mmol, 73%) of the title compound as a brownish solid.

HPLC (AUC, Merck Chromolith Performance RP18e, A. H$_2$O/0.05% TFA, B: MeCN/0.05% TFA, 10->70% B in 7 min, 4 ml/min, 40° C., UV: 210 nm): $R_t$=3.00 min; LC-MS: (YMC J' sphere ODS H 80 20×2.1 mm, 4 μm, A: H$_2$O+0.05% TFA, B: MeCN, 4%→95% B in 2 min, 1 ml/min, 30° C., UV: 220 nm; MS: ESI): $R_t$=1.11 min, MH$^+$ 499; NMR (400 MHz): 1.15-1.26 (m, 2H), 1.36-1.50 (m, 2H), 1.45 (s, 6H, 2×CH$_3$), 1.73 (q, 2H), 1.80-1.92 (m, 2H), 2.21-2.30 (m, 2H), 2.39-2.50 (m, 1H), 2.78-2.87 (m, 2H), 2.96 (t, 2H), 5.12 (s, 1H, OH), 6.94 (bs, 2H, NH2), 7.08-7.14 (m, 2H, Ar—H), 7.21-7.29 (m, 4H, Ar—H), 7.42-7.47 (m, 2H, Ar—H), 7.47-7.54 (m, 4H, Ar—H), 7.85-7.92 (m, 2H, Ar—H); mp: 176-178° C. (BuOH/MeOH/water).

Example 7

2-(4-{1-Hydroxy-4-[4-(hydroxy-diphenyl-methyl)-piperidin-1-yl]-butyl}-phenyl)-isobutyramide of the Formula VI-B after Coupling without any Catalyst and In Situ Reduction 4.01 g (17.3 mmol, 1.1 eq.) 2-[4-(cyclopropanecarbonyl)phenyl]-2-methyl-propanamide of the formula V-B, 4.21 g (15.8 mmol, 1.0 eq.) azacyclonol and 0.5 ml (5 wt %) mesitylene were stirred for 16 h at 175° C. The mixture was cooled to 120° C. and BuOH (6 ml) was added. The mixture was then cooled to 60° C. and 6 ml MeOH and 2 ml water were added and the mixture was cooled to rt. Sodium borohydride (328 mg, 8.63 mmol, 0.5 eq.) was added in portions and mixture was stirred 2 h at rt. The formed solid was crystallised from 60 ml MeOH/water 3:2 to yield 5.51 g (11.0 mmol, 70%) of the title compound as a white solid.

HPLC (AUC, Merck Chromolith Performance RP18e, A. H$_2$O/0.05% TFA, B: MeCN/0.05% TFA, 10->70% B in 7 min, 4 ml/min, 40° C., UV: 210 nm): R$_t$=2.71 min; LC-MS: (YMC J' sphere ODS H 80 20×2.1 mm, 4 μm, A: H$_2$O+ 0.05% TFA, B: MeCN, 4%→95% B in 2 min, 1 ml/min, 30° C., UV: 220 nm; MS: ESI): R$_t$=1.02 min, MH$^+$ 501; NMR (400 MHz): 1.15-1.26 (m, 2H), 1.29-1.61 (m, 6H), 1.41 (s, 6H, 2×CH$_3$), 1.76-1.89 (m, 2H), 2.12-2.26 (m, 2H), 2.39-2.50 (m, 1H), 2.73-2.87 (m, 2H), 4.41-4.51 (m, 1H, CHOH), 5.20 (s, 1H, OH), 5.34 (d, 1H, CHOH), 6.82 (bs, 2H, NH2), 7.08-7.15 (m, 2H, Ar—H), 7.19-7.29 (m, 8H, Ar—H), 7.46-7.53 (m, 4H, Ar—H); mp: 194° C. (MeOH/water).

Example 8

2-(4-{1-Hydroxy-4-[4-(hydroxy-diphenyl-methyl)-piperidin-1-yl]-butyl}-phenyl)-isobutyramide of the Formula VI-B with CaCl$_2$) as Catalyst and Subsequent Reduction 9.99 g (43.2 mmol, 1.1 eq.) 2-[4-(cyclopropanecarbonyl)phenyl]-2-methyl-propanamide of formula V-B, 10.5 g (39.3 mmol, 1.0 eq.) azacyclonol and Calcium chloride (870 mg, 7.85 mmol, 0.2 eq.) were stirred in 2 ml (8 wt %) p-xylene for 17 h at 145° C. The mixture was cooled to 110° C. and toluene (120 ml), EtOH (60 ml) and water (8 ml) were added. The mixture was then cooled to rt and sodium borohydride (817 mg, 21.6 mmol, 0.55 eq.) was added in portions and the mixture was stirred 1 h at rt. The mixture was heated to 70° C., the mixture was filtered and ethanol was removed by distillation. After cooling to rt the formed solid was filtered to yield 16.4 g (32.7 mmol, 83%) of the title compound as a white solid.

HPLC (AUC, Merck Chromolith Performance RP18e, A. H$_2$O/0.05% TFA, B: MeCN/0.05% TFA, 10->70% B in 7 min, 4 ml/min, 40° C., UV: 210 nm): R$_t$=2.68 min; LC-MS: (YMC J' sphere ODS H 80 20×2.1 mm, 4 μm, A: H$_2$O+ 0.05% TFA, B: MeCN, 4%→95% B in 2 min, 1 ml/min, 30° C., UV: 220 nm; MS: ESI): R$_t$=1.01 min, MH$^+$ 501.

Example 9

2-(4-{1-Hydroxy-4-[4-(hydroxy-diphenyl-methyl)-piperidin-1-yl]-butyl}-phenyl)-isobutyramide of Formula VI-B with LiCl as the Catalyst and Subsequent Reduction 3.96 g (17.1 mmol, 1.1 eq.) 2-[4-(cyclopropanecarbonyl)phenyl]-2-methyl-propanamide of formula V-B, 4.16 g (15.6 mmol, 1.0 eq.) azacyclonol and Lithium chloride (200 mg, 4.67 mmol, 0.3 eq.) were stirred in 1 ml (10 wt %) p-xylene for 18 h at 145° C. The mixture was cooled to 110° C. and toluene (20 ml), EtOH (10 ml) and water (3 ml) were added. The mixture was then cooled to rt and sodium borohydride (324 mg, 8.56 mmol, 0.55 eq.) was added in portions and mixture was stirred 1 h at rt. The mixture was heated to 70° C., the mixture was filtered and ethanol was removed by distillation. After cooling to rt the formed solid was filtered to yield 6.64 g (13.3 mmol, 85%) of the title compound as a white solid. Analytical data were identical with those obtained in example 7 and 8.

Example 10

2-(4-{1-Hydroxy-4-[4-(hydroxy-diphenyl-methyl)-piperidin-1-yl]-butyl}-phenyl)-2-methyl-propionitrile of Formula VI-A by Reduction of Compound of Formula II-A Compound II-A (4.00 g, 8.32 mmol) was dissolved in 30 ml BuOH and 2 ml water. NaBH4 (126 mg, 3.33 mmol, 0.4 eq.) was added in portions and the mixture was heated to 70° C. for 4 h. The mixture was extracted with water (2×10 ml) and was slowly cooled to rt. The solid was filtered at 0° C., washed with cold BuOH and the title compound was obtained as a white solid (3.67 g, 7.57 mmol, 91%).

HPLC (AUC, Merck Chromolith Performance RP18e, A. H$_2$O/0.05% TFA, B: MeCN/0.05% TFA, 25->50% B in 6 min, 4 ml/min, 40° C., UV: 210 nm): R$_t$=3.30 min; LC-MS: (Waters UPLC BEH C18 50×2.1 mm, 1.7 μm, A: H$_2$O+ 0.05% TFA, B: MeCN/0.035% TFA, 5%→95% B in 2 min, 0.9 ml/min, 55° C., UV: 220 nm; MS: ES): R$_t$=1.55 min, M$^+$ 482; NMR (400 MHz): 1.16-1.26 (m, 2H), 1.29-1.60 (m, 6H), 1.66 (s, 6H, 2×CH$_3$), 1.76-1.89 (m, 2H), 2.20 (t, 2H), 2.38-2.49 (m, 1H), 2.75-2.85 (m, 2H), 4.46-4.55 (m, 1H), 5.20 (s, 1H, OH), 5.47 (d, 1H, OH), 7.08-7.15 (m, 2H, Ar—H), 7.31-7.37 (m, 2H, Ar—H), 7.40-7.46 (m, 2H, Ar—H), 7.47-7.53 (m, 4H, Ar—H); mp: 179° C. BuOH/water).

Example 11

2-(4-{1-Hydroxy-4-[4-(hydroxy-diphenyl-methyl)-piperidin-1-yl]-butyl}-phenyl)-2-methyl-propionitrile of Formula VI-A by Coupling of Compound V-A with Compound of Formula IV and In Situ Reduction Azacyclonol (5.34 g, 20.0 mmol), 2-[4-(cyclopropanecarbonyl-)-phenyl]-2-methyl-propanenitrile of formula V-A (4.69 g, 22.0 mmol, 1.1 eq) and LiCl (0.42 g, 10 mmol, 0.5 eq.) and 1 ml (8 wt %) p-xylene were stirred for 22 h at 150° C. The mixture was cooled to 110° C., diluted with 30 ml toluene and extracted with 10 ml water/2% AcOH. Toluene (20 ml), EtOH (30 ml) and water (4 ml) were added followed by NaBH4 (460 mg, 12 mmol, 0.6 eq). The mixture was stirred for 80 min, 20 ml toluene were added and the solid was filtered and dried to yield 6.90 g (14.3 mmol, 72%) of the title compound as a white solid.

HPLC (AUC, Merck Chromolith Performance RP18e, A. $H_2O$/0.05% TFA, B: MeCN/0.05% TFA, 25->50% B in 6 min, 4 ml/min, 40° C., UV: 210 nm): $R_t$=3.31 min; LC-MS: (YMC J' sphere ODS H 80 20×2.1 mm, 4 μm, A: $H_2O$+ 0.05% TFA, B: MeCN, 4%→95% B in 2 min, 1 ml/min, 30° C., UV: 220 nm; MS: ESI): $R_t$=1.18 min, $MH^+$ 483.; mp: 178° C. (EtOH/toluene/water).

Example 12

Fexofenadine Sodium Salt of Compound of Formula I by Hydrolysis of the Compound of Formula VI-A 2-(4-{1-Hydroxy-4-[4-(hydroxy-diphenyl-methyl)-piperidin-1-yl]-butyl}-phenyl)-2-methyl-propionitrile of formula VI-A (6.00 g, 12.4 mmol) and NaOH (3.48 g, 87.0 mmol, 7 eq.) in 2 ml water and 16 ml butanol were refluxed for 10 h. The mixture was cooled to 100° C. and extracted with 10 ml water and 10 ml aq. $NaHCO_3$. After cooling to rt butyl acetate (30 ml) was added and mixture was distilled (75 mbar/50° C.). The precipitate was collected to yield the title compound (6.6 g, among with some sodium carbonate) as a white solid.

HPLC (AUC, Merck Chromolith Performance RP18e, A. $H_2O$/0.05% TFA, B: MeCN/0.05% TFA, 10->70% B in 7 min, 4 ml/min, 40° C., UV: 210 nm): $R_t$=3.57 min; LC-MS: (YMC J' sphere ODS H 80 20×2.1 mm, 4 μm, A: $H_2O$+ 0.05% TFA, B: MeCN, 4%→95% B in 3.8 min, 1 ml/min, 30° C., UV: 220 nm; MS: ESI): $R_t$=1.19 min, $MH^+$ 502; mp: 217-219° C. (BuOH/butyl acetate)

Example 13

Fexofenadine Hydrochloride Salt from Fexofenadine Sodium Salt

Fexofenadine sodium salt (2.00 g, 3.82 mmol) was suspended in 5.5 ml MeOH and 5.5 ml water. Conc. HCl was added until pH of about 2. The mixture was cooled to 0° C. and the solid was filtered and dried in vacuum at 40° C. 1.79 g (3.21 mmol, 84%) of the title compound were obtained as a white solid.

HPLC (AUC, Merck Chromolith Performance RP18e, A. $H_2O$/0.05% TFA, B: MeCN/0.05% TFA, 10->70% B in 7 min, 4 ml/min, 40° C., UV: 210 nm): $R_t$=3.78 min; LC-MS: (Waters UPLC BEH C18 50×2.1 mm, 1.7 μm, A: $H_2O$+ 0.05% TFA, B: MeCN/0.035% TFA, 5%→95% B in 2 min, 0.9 ml/min, 55° C., UV: 220 nm; MS: ES): $R_t$=1.50 min, $M^+$ 501; LC-MS: (YMC J' sphere ODS H 80 20×2.1 mm, 4 μm, A: $H_2O$+0.05% TFA, B: MeCN, 4%→95% B in 3.8 min, 1 ml/min, 30° C., UV: 220 nm; MS: ESI): $R_t$=1.11 min, $MH^+$ 502;

NMR (400 MHz): 1.36-1.52 (m, 2H), 1.45 (s, 6H, 2×$CH_3$), 1.53-1.83 (m, 6H), 2.76-3.03 (m, 5H), 3.36-3.47 (m, 2H), 4.48-4.57 (m, 1H, CHOH), 5.25-5.33 (m, 1H, OH), 5.63 (s, 1H, OH), 7.11-7.20 (m, 2H, Ar—H), 7.24-7.35 (m, 8H, Ar—H), 7.45-7.57 (m, 4H, Ar—H), 9.40 (bs, 1H), 12.3 (bs, 1H); mp:

Example 14

Fexofenadine of Formula I by Hydrolysis of the Compound of Formula VI-B and Formation of the Hydrochloride Salt 2-(4-{1-Hydroxy-4-[4-(hydroxy-diphenyl-methyl)-piperidin-1-yl]-butyl}-phenyl)-isobutyramide of the formula VI-B (1.50 g, 3.00 mmol) was added to NaOH (360 mg, 8.99 mmol) in 15 ml butanol. The mixture was refluxed for 20 h. After cooling to the pH was adjusted to about 7 with 32% aq. HCl, ethyl acetate (15 ml) was added and the solid was filtered to yield the title compound (1.12 g, 2.23 mmol, 75% yield) as a white solid.

HPLC (AUC, Merck Chromolith Performance RP18e, A. $H_2O$/0.05% TFA, B: MeCN/0.05% TFA, 10->70% B in 7 min, 4 ml/min, 40° C., UV: 210 nm): $R_t$=3.05 min; LC-MS: (YMC J' sphere ODS H 80 20×2.1 mm, 4 μm, A: $H_2O$+ 0.05% TFA, B: MeCN, 4%→95% B in 2 min, 1 ml/min, 30° C., UV: 220 nm; MS: ESI): $R_t$=1.63 min, $MH^+$ 502.

Example 15

Fexofenadine of Formula I by Direct Reduction/Nitril Hydrolysis of the Compound of Formula II-A and Formation of the Hydrochloride Salt 2-[4-[4-[4-[hydroxy(diphenyl)methyl]-1-piperidyl]butanoyl]phenyl]-2-methyl-propanenitrile of formula II-A (25.0 g, 52.0 mmol) was added to NaOH (4.16 g, 104 mmol) in 4 ml water and 100 ml 2-butanol. The mixture was refluxed for 8 h. 2-BuOH (25 ml) and MeOH (25 ml) were added and the mixture was heated for 20 h at 130° C. under pressure. HPLC analysis revealed the formation of 97% product. An ⅕ aliquot of the solution was taken and treated with 32% aq. HCl until pH 2. Water (20 ml) was added and the mixture was cooled to 0° C. The solid was filtered and dried in vacuum to yield Fexofenadine hydrochloride (4.62 g, 8.60 mmol, 83% yield) as a white solid.

HPLC (AUC, Merck Chromolith Performance RP18e, A. $H_2O$/0.05% TFA, B: MeCN/0.05% TFA, 10->70% B in 7 min, 4 ml/min, 40° C., UV: 210 nm): $R_t$=3.78 min; LC-MS: (YMC J' sphere ODS H 80 20×2.1 mm, 4 μm, A: $H_2O$+ 0.05% TFA, B: MeCN, 4%→95% B in 2 min, 1 ml/min, 30° C., UV: 220 nm; MS: ESI): $R_t$=1.12 min, $MH^+$ 502.

Example 16

2-[4-[4-[4-[hydroxyl(diphenyl)methyl]-1-piperidinyl]butanoyl]phenyl]2-methyl-propanoic Acid of Formula VII as Sodium Salt by Coupling of 2-[4-(cyclopropanecarbonyl-)-phenyl]-2-methyl-propanoic Acid Ethylester of Formula V-C (R1 is COOEt) with Azacyclonol Followed by Hydrolysis of the Ester General procedure for preparing 2-[4-[4-[4-[hydroxyl(diphenyl)methyl]-1-piperidinyl]butanoyl]phenyl]2-methyl-propanoic acid sodium salt of formula VII using azacyclonol (Diphenyl(piperidin-4-yl)methanol, CAS: 115-46-8), 2-[4-(cyclopropanecarbonyl-)-phenyl]-2-methyl-propanoic acid ethylester of formula V-C and different salts as catalysts to obtain compound 2-[4-[4-[4-[hydroxyl(diphenyl)methyl]-1-piperidinyl]butanoyl]phenyl]2-methyl-propanoic acid ethylester of formula II-C (R1 is ethyl) followed by hydrolysis to obtain 2-[4-[4-[4-[hydroxyl(diphenyl)methyl]-1-piperidinyl]butanoyl]phenyl]2-methyl-propionic acid of formula VII as sodium salt:

Coupling: Azacyclonol (2.67 g, 10.0 mmol) and 2-[4-(cyclopropanecarbonyl-)-phenyl]-2-methyl-propanoic acid ethylester (2.6 g, 10.0 mmol) were placed in a 25 ml 3-necked flask. Toluene (0.2 ml, 3 wt %) and catalyst as specified below were added and the mixture were heated to 140° C. and stirred as specified in the single experiments.

The conversion was monitored by HPLC until almost complete. HPLC (AUC, Merck Chromolith Performance RP18e, A: H$_2$O/0.05% TFA, B: MeCN/0.05% TFA, 25->50% B in 7 min, 50->70% B from 7 min to 9 min., 4 ml/min, 40° C., UV: 210 nm).

Hydrolysis to the sodium salt: The mixtures were cooled to 110° C., EtOH (20 ml) and water (4 ml) was added carefully and the mixture was cooled down to about 25° C. with stirring. 1.89 ml 32% aq. NaOH (2 eq) was added with cooling and the mixture was heated to 50° C. and stirred for 6 h. Hydrolysis of the ester was monitored by HPLC (AUC). A sample was taken after hydrolysis. The mixture was cooled to about 25° Ct and water (5 ml) was added. The ethanol was removed by distillation. The remaining aq. solution was extracted with n-BuOH (30 ml), the phases separated and the organic phase was extracted two times with 10 ml aq. NaHCO$_3$ and one time with 5 ml water. n-butylacetate (30 ml) was added and the mixture was destilled (75 mbar/50° C.). The solid was filtered and washed with n-butylacetate to yield the sodium salt of the title compound VII as a white solid. The products were characterized by HPLC (AUC, Merck Chromolith Performance RP18e, A: H$_2$O/0.05% TFA, B: MeCN/0.05% TFA, 25->50% B in 7 min, 50->70% B from 7 min to 9 min., 4 ml/min, 40° C., UV: 210 nm) and LC-MS: (YMC J'sphere ODS H 80×20×2.1 mm, 4 μm, A: H$_2$O+0.05% TFA, B: MeCN, 4%->95% B in 2 min., 1 ml/min, 30° C., UV: 220 nm; MS: ESI).

Example A

The reaction was performed as described in the general procedure with 0.21 g (2.0 mmol, 0.2 equivalents) lithium perchlorate (CAS: 7791-03-9) from Sigma Aldrich for 6 h at 140° C. After hydrolysis the compound VII was isolated according to the general procedure (4.24 g; purity 85%; 69% yield).

The isolated solid was characterized by HPLC (method as described above, Rt=2.92 min) and LC-MS: Rt=1.41 min, MH$^+$ 500

Example B

The reaction was performed as described in the general procedure with 0.54 g (2.0 mmol, 0.2 equivalents) barium perchlorate (CAS: 13465-95-7) from ABCR for 6 h at 140° C. After hydrolysis the compound VII was isolated according to the general procedure to yield 3.3 g (purity 92%; 58% yield).

The isolated solid was characterized by HPLC (method as described above, Rt=2.92 min) and LC-MS: Rt=1.41 min, MH$^+$ 500.

Example C

The reaction was performed as described in the general procedure 0.31 g (2.0 mmol, 0.2 equivalents) lithium triflate (CAS: 33454-82-9) from Sigma Aldrich for 6 h at 140° C. After hydrolysis the compound VII was isolated according to the general procedure to yield 4.06 g (purity 89%; 69% yield).

The isolated solid was characterized by HPLC (method as described above, Rt=2.92 min) and LC-MS: Rt=1.41 min, MH$^+$ 500.

The invention claimed is:

1. A process for preparing a compound of formula II

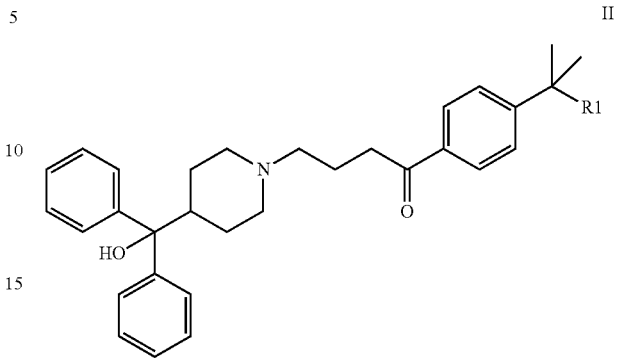

wherein R1 is CN, CONH$_2$, or COOR2, wherein R2 is C1-4 alkyl, comprising reacting a compound of formula V

V wherein R1 is CN, CONH$_2$ or COOR2, wherein R2 is C1-4 alkyl, with the compound of formula IV

IV at a temperature above 80° C. without any solvent or at a temperature above 80° C. in the presence of an amount of solvent up to 50 wt % of the sum of the weights of the compound of formula V and the compound of formula IV, and in the presence of a salt, wherein the salt is a lithium, sodium, potassium, rubidium, caesium, magnesium, calcium, strontium, barium, scandium, manganese, iron, copper, zinc, silver, boron, aluminium, gallium, indium, cerium, europium, ytterbium or bismuth salt, to form the compound of formula II.

2. The process according to claim 1, wherein the amount of solvent is up to 20 wt % of the sum of the weights of the compound of formula V and the compound of formula IV.

3. The process according to claim 1, wherein when R1 is COOR2, the temperature is in the range of 80 to 150° C.

4. The process according to claim 1, wherein when R1 is CN or CONH$_2$, the temperature is in the range of 80 to 350° C.

5. The process according to claim 1, wherein the salt is a lithium, sodium, magnesium, calcium, barium, scandium, manganese, iron, copper, silver, zinc, aluminium, gallium, indium, cerium, europium, ytterbium or bismuth salt.

6. The process according to claim 1, wherein the salt is a lithium, sodium, calcium, barium, magnesium, silver, europium or iron salt.

7. The process according to claim 1, wherein the salt is a lithium salt.

8. The process according to claim 1, wherein the anion in the salt is selected from the group consisting of chloride, bromide, iodide, perchlorate, nitrate, trifluoromethanesulfonate and trifluoroacetate.

9. The process according to claim 1, wherein the salt is selected from the group consisting of lithium perchlorate, lithium trifluoromethanesulfonate, lithium bromide, lithium tifluoroacetate, lithium nitrate, lithium iodide, barium perchlorate, barium trifluoromethanesulfonate, calcium trifluoromethanesulfonate, and sodium trifluoromethanesulfonate.

10. A process for preparing a compound of formula I

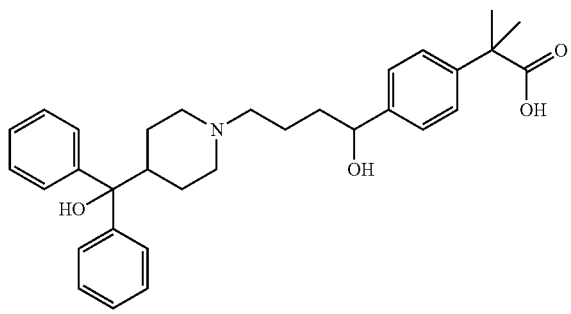

I or a pharmaceutically acceptable salt thereof
  comprising:
    preparing the compound of formula II according to claim 1,
    and converting the compound of formula II into the compound of formula I or a pharmaceutically acceptable salt thereof.

11. The process according to claim 10, wherein the compound of formula II is converted into the compound of formula I by sequentially or simultaneously reducing the ketone moiety and hydrolyzing the nitrile, the amide, or the ester moiety in R1 of the compound of formula II.

12. The process according to claim 11, wherein the compound of formula II is first reduced to a compound of formula VI

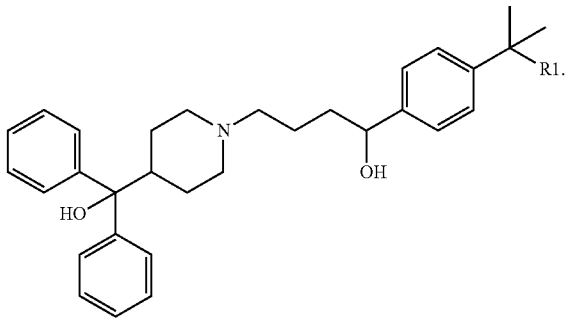

VI

13. The process according to claim 12, wherein the compound of formula II prepared is not isolated and is directly converted into the compound of formula VI.

14. The process according to claim 11, wherein the compound of formula II is converted into the compound of formula I by simultaneously reducing the ketone moiety and hydrolyzing the nitrile, the amide or the ester moiety in R1 of the compound of formula II.

15. The process according to claim 10, wherein the compound of formula I is converted into a pharmaceutically acceptable salt thereof.

16. The process according to claim 1, wherein R1 is CN.

17. The process according to claim 1, wherein the salt is lithium perchlorate.

18. A compound of formula II-B having the following structure:

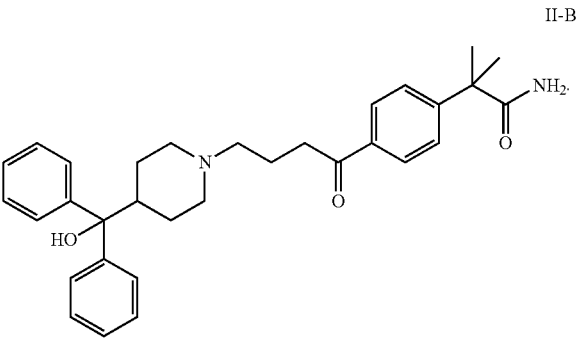 [SMILES: CC(C)(C(N)=O)c1ccc(C(=O)CCCN2CCC(C(O)(c3ccccc3)c3ccccc3)CC2)cc1]

II-B

* * * * *